(12) United States Patent
Hiramatsu et al.

(10) Patent No.: US 11,448,628 B2
(45) Date of Patent: Sep. 20, 2022

(54) SENSOR AND SENSOR MODULE

(71) Applicant: KABUSHIKI KAISHA TOSHIBA, Tokyo (JP)

(72) Inventors: Naoki Hiramatsu, Yokohama Kanagawa (JP); Yosuke Akimoto, Yokohama Kanagawa (JP); Hiroaki Yamazaki, Yokohama Kanagawa (JP); Yumi Hayashi, Ayase Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 34 days.

(21) Appl. No.: 17/183,022

(22) Filed: Feb. 23, 2021

(65) Prior Publication Data

US 2022/0018820 A1 Jan. 20, 2022

(30) Foreign Application Priority Data

Jul. 17, 2020 (JP) .............................. JP2020-122799

(51) Int. Cl.
*G01N 27/22* (2006.01)
*G01N 33/00* (2006.01)
(Continued)

(52) U.S. Cl.
CPC ......... *G01N 33/005* (2013.01); *G01N 27/045* (2013.01); *G01N 27/18* (2013.01);
(Continued)

(58) Field of Classification Search
CPC .... G01N 33/005; G01N 27/045; G01N 27/18; G01N 27/226; G01N 27/228; G01N 2027/222
See application file for complete search history.

(56) References Cited

U.S. PATENT DOCUMENTS 4,706,014 A * 11/1987 Fabbri .................. G01N 27/226
324/684
11,085,836 B2 * 8/2021 Okada ..................... G01L 25/00
(Continued)

FOREIGN PATENT DOCUMENTS

JP 2019-56607 A 4/2019
JP 2020-41893 A 3/2020

*Primary Examiner* — David J Bolduc
(74) *Attorney, Agent, or Firm* — Finnegan, Henderson, Farabow, Garrett & Dunner L.L.P.

(57) ABSTRACT

According to one embodiment, a sensor includes a base body, and a first sensor part. The first sensor part includes fixed and movable electrode members, and first and second support members. The fixed electrode member includes a fixed electrode fixed to the base body. The movable electrode member includes a movable electrode. The movable electrode member includes first and second movable portions, and a third movable portion between the first and second movable portions. The first support member is fixed to the base body and connected with the first movable portion. The second support member is fixed to the base body and connected with the second movable portion. The first and second support members support the movable electrode member to provide a first gap between the fixed and movable electrode members. The fixed electrode member includes first, second, and third fixed electrode portions facing the movable portion.

20 Claims, 16 Drawing Sheets

(51) Int. Cl.
*G01N 27/18* (2006.01)
*G01N 27/04* (2006.01)
(52) U.S. Cl.
CPC ......... *G01N 27/226* (2013.01); *G01N 27/228*
(2013.01); *G01N 2027/222* (2013.01)

(56) References Cited

U.S. PATENT DOCUMENTS

| | | | |
|---|---|---|---|
| 2008/0265710 A1* | 10/2008 | Ikehashi | H01G 5/16 |
| | | | 310/309 |
| 2010/0072563 A1* | 3/2010 | Sato | B81B 7/007 |
| | | | 257/E29.324 |
| 2014/0284767 A1* | 9/2014 | Yamazaki | H01G 5/18 |
| | | | 257/600 |
| 2019/0086377 A1 | 3/2019 | Ikehashi et al. | |
| 2020/0080954 A1 | 3/2020 | Yamazaki | |
| 2020/0408708 A1* | 12/2020 | Geier | G01N 27/226 |

* cited by examiner

SENSOR AND SENSOR MODULE

CROSS-REFERENCE TO RELATED APPLICATIONS

This application is based upon and claims the benefit of priority from Japanese Patent Application No. 2020-122799, filed on Jul. 17, 2020; the entire contents of which are incorporated herein by reference.

FIELD

Embodiments described herein relate generally to a sensor and a sensor module.

BACKGROUND

For example, there is a sensor that detects a gas such as hydrogen, etc. It is desirable to increase the detection sensitivity of the sensor.

DETAILED DESCRIPTION

Figure 1A:
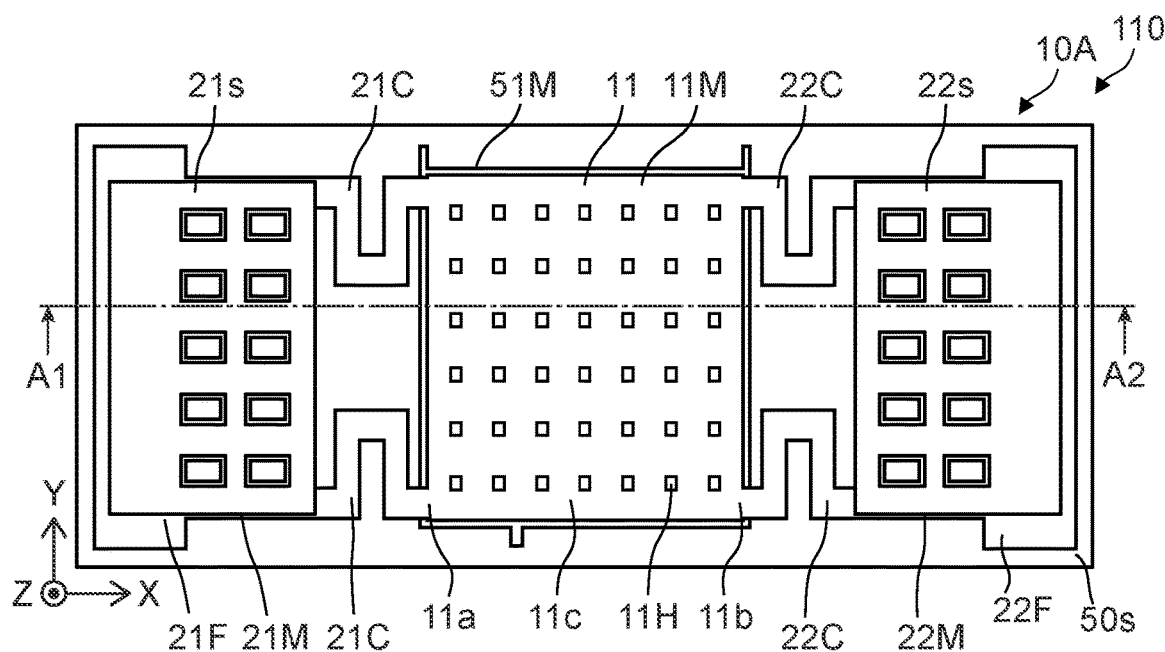
FIGS. 1A and 1B are schematic views illustrating a sensor according to a first embodiment.

According to one embodiment, a sensor includes a base body, and a first sensor part. The first sensor part includes a fixed electrode member, a movable electrode member, a first support member, and a second support member. The fixed electrode member includes a fixed electrode fixed to the base body. The movable electrode member includes a movable electrode. The movable electrode member includes a first movable portion, a second movable portion, and a third movable portion between the first movable portion and the second movable portion. The first support member is fixed to the base body and connected with the first movable portion. The second support member is fixed to the base body and connected with the second movable portion. The first and second support members support the movable electrode member to provide a first gap between the fixed electrode member and the movable electrode member. The fixed electrode member includes a first fixed electrode portion facing the first movable portion, a second fixed electrode portion facing the second movable portion, and a third fixed electrode portion facing the third movable portion. A third distance along a first direction between the third fixed electrode portion and the third movable portion is less than a first distance along the first direction between the first fixed electrode portion and the first movable portion and less than a second distance along the first direction between the second fixed electrode portion and the second movable portion. The first direction is from the fixed electrode member toward the movable electrode member.

According to one embodiment, a sensor includes a base body, and a first sensor part. The first sensor part includes a fixed electrode member, a movable electrode member, a first support member, and a second support member. The fixed electrode member includes a fixed electrode fixed to the base body. The movable electrode member includes a movable electrode. The movable electrode member includes a first movable portion, a second movable portion, and a third movable portion between the first movable portion and the second movable portion. The first support member is fixed to the base body and connected with the first movable portion. The second support member is fixed to the base body and connected with the second movable portion. The first and second support members support the movable electrode member to provide a first gap between the fixed electrode member and the movable electrode member. The first support member includes a first fixed part-side portion and a first connection part-side portion. The first connection part-side portion is between the first fixed part-side portion and the first movable portion. A distance along the first direction between the base body and the first connection part-side portion is greater than a distance along the first direction between the base body and the first fixed part-side portion.

According to one embodiment, a sensor includes a base body, and a sensor part. The sensor part includes a sensor member, a first support part, and a second support part. The sensor member includes a conductive member. The sensor member includes a first sensor portion, a second sensor portion, and a third sensor portion between the first sensor portion and the second sensor portion. The first support part is fixed to the base body and connected with the first sensor portion. The second support part is fixed to the base body and connected with the second sensor portion. The first and second support parts support the sensor member to provide a second gap between the base body and the sensor member. The base body includes a first counter portion facing the first sensor portion, a second counter portion facing the second sensor portion, and a third counter portion facing the third sensor portion. A third counter distance along the first direction between the third counter portion and the third sensor portion is greater than a first counter distance along the first direction between the first counter portion and the first sensor portion and greater than a second counter distance along the first direction between the second counter portion and the second sensor portion.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
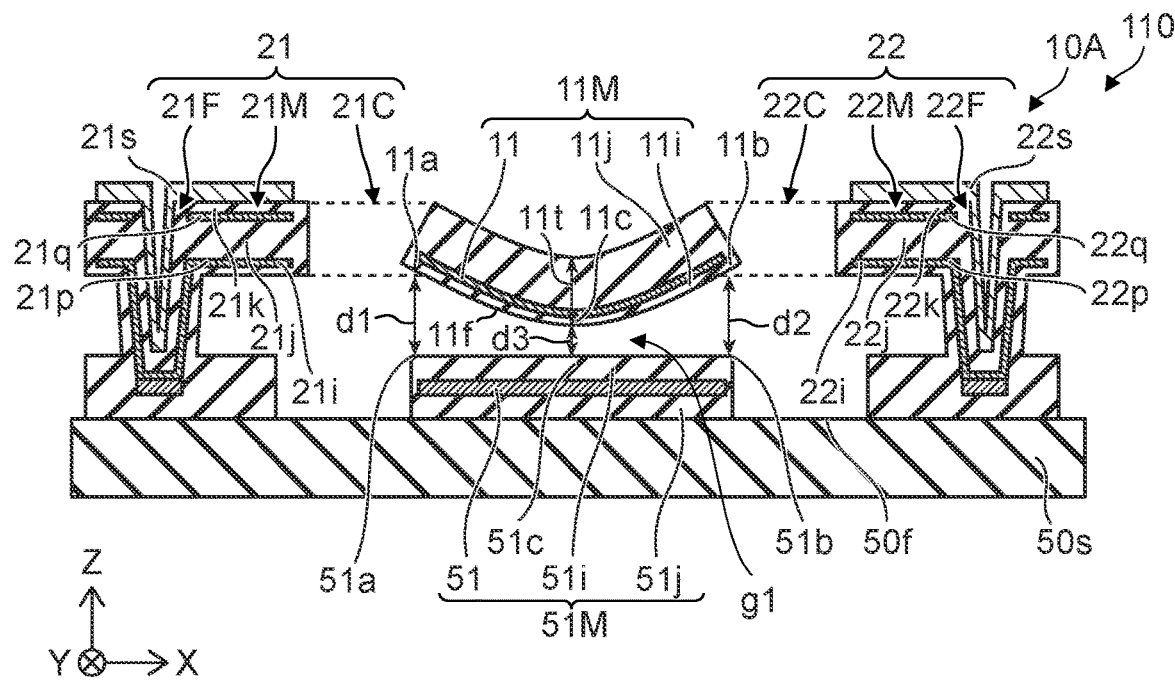

FIGS. 1A and 1B are schematic views illustrating a sensor according to a first embodiment.

FIG. 1A is a plan view. FIG. 1B is a line A1-A2 cross-sectional view of FIG. 1A.

As shown in FIGS. 1A and 1B, the sensor 110 according to the embodiment includes a base body 50s and a first sensor part 10A. The base body 50s is, for example, a substrate. The base body 50s may be, for example, a semiconductor substrate (e.g., a silicon substrate, etc.).

The first sensor part 10A includes a fixed electrode member 51M, a movable electrode member 11M, a first support member 21, and a second support member 22.

The fixed electrode member 51M includes a fixed electrode 51. The fixed electrode 51 is fixed to the base body 50s. In the example, the fixed electrode member 51M includes an insulating region 51i and an insulating region 51j. The fixed electrode 51 is located between the base body 50s and the insulating region 51i. The insulating region 51j is located between the base body 50s and the fixed electrode 51.

The movable electrode member 11M includes a first movable portion 11a, a second movable portion 11b, and a third movable portion 11c. The third movable portion 11c is between the first movable portion 11a and the second movable portion 11b. For example, at least a portion of the fixed electrode member 51M is between the movable electrode member 11M and a portion of the base body 50s.

A first direction from the fixed electrode member 51M toward the movable electrode member 11M is taken as a Z-axis direction. One direction perpendicular to the Z-axis direction is taken as an X-axis direction. A direction perpendicular to the Z-axis direction and the X-axis direction is taken as a Y-axis direction.

For example, the base body 50s includes a base body surface 50f. The base body surface 50f is, for example, the upper surface. The base body surface 50f is substantially parallel to the X-Y plane. The base body surface 50f is substantially perpendicular to the first direction (the Z-axis direction). The fixed electrode member 51M is located on the base body surface 50f.

As shown in FIG. 1B, the first support member 21 is fixed to the base body 50s and connected with the first movable portion 11a. In the example, the first support member 21 includes a first fixed part 21F, a first intermediate support part 21M, and a first connection part 21C. The first fixed part 21F is fixed to the base body 50s. The first connection part 21C is connected with the first movable portion 11a of the movable electrode member 11M. The first intermediate support part 21M is between the first fixed part 21F and the first connection part 21C. The first intermediate support part 21M and the first connection part 21C are separated from the base body 50s. A gap is between the base body 50s and the first intermediate support part 21M. A gap is between the base body 50s and the first connection part 21C. The first fixed part 21F, the first intermediate support part 21M, and the first connection part 21C may be continuous with each other. The first connection part 21C is, for example, a spring part.

As shown in FIG. 1B, the second support member 22 is fixed to the base body 50s and connected with the second movable portion 11b. In the example, the second support member 22 includes a second fixed part 22F, a second intermediate support part 22M, and a second connection part 22C. The second fixed part 22F is fixed to the base body 50s. The second connection part 22C is connected with the second movable portion 11b of the movable electrode member 11M. The second intermediate support part 22M is between the second fixed part 22F and the second connection part 22C. The second intermediate support part 22M and the second connection part 22C are separated from the base body 50s. A gap is between the base body 50s and the second intermediate support part 22M. A gap is between the base body 50s and the second connection part 22C. The second fixed part 22F, the second intermediate support part 22M, and the second connection part 22C may be continuous with each other. The second connection part 22C is, for example, a spring part.

In the example as shown in FIGS. 1A and 1B, the direction from the first support member 21 toward the second support member 22 is along the X-axis direction. The movable electrode member 11M is between the first support member 21 and the second support member 22 in the X-axis direction. The first intermediate support part 21M is between the first fixed part 21F and the movable electrode member 11M in the X-axis direction. The first connection part 21C is between the first intermediate support part 21M and the movable electrode member 11M in the X-axis direction. The second intermediate support part 22M is between the movable electrode member 11M and the second fixed part 22F in the X-axis direction. The second connection part 22C is between the movable electrode member 11M and the second intermediate support part 22M in the X-axis direction.

The direction from the first fixed part 21F toward the movable electrode member 11M is along a second direction (e.g., the X-axis direction). The second direction crosses the first direction (the Z-axis direction). A direction that crosses a plane including the first direction (the Z-axis direction) and the second direction (the X-axis direction) is taken as a third direction. The third direction is, for example, the Y-axis direction. As shown in FIG. 1A, the length along the third direction (e.g., the Y-axis direction) of at least a portion of the first connection part 21C is less than the length along the third direction of the first intermediate support part 21M. For example, the length along the third direction of at least a portion of the second connection part 22C is less than the length along the third direction of the second intermediate support part 22M.

Multiple first connection parts 21C and multiple second connection parts 22C may be provided as shown in FIG. 1A. The direction from one of the multiple first connection parts 21C toward another one of the multiple first connection parts 21C is along the Y-axis direction. The direction from one of the multiple second connection parts 22C toward another one of the multiple second connection parts 22C is along the Y-axis direction.

As shown in FIG. 1B, the first and second support members 21 and 22 support the movable electrode member 11M to provide a first gap g1 between the fixed electrode member 51M and the movable electrode member 11M.

As shown in FIG. 1B, the movable electrode member 11M is warped. For example, the movable electrode member 11M includes a first movable surface 11f. The first movable surface 11f faces the fixed electrode member 51M. The first movable surface 11f is, for example, the lower surface. The first movable surface 11f is convex. For example, the first movable surface 11f is warped to be convex toward the fixed electrode member 51M.

For example, the fixed electrode member 51M includes a first fixed electrode portion 51a facing the first movable portion 11a, a second fixed electrode portion 51b facing the second movable portion 11b, and a third fixed electrode portion 51c facing the third movable portion 11c. The distance along the first direction (the Z-axis direction) between the first fixed electrode portion 51a and the first movable portion 11a is taken as a first distance d1. The distance along the first direction (the Z-axis direction) between the second fixed electrode portion 51b and the second movable portion 11b is taken as a second distance d2. The distance along the first direction (the Z-axis direction) between the third fixed electrode portion 51c and the third movable portion 11c is taken as a third distance d3.

According to the embodiment, the third distance d3 is less than the first distance d1 and less than the second distance d2.

Due to such a configuration, high detection sensitivity is easily obtained. For example, as described below, the shapes of the first and second support members 21 and 22 change according to the concentration of a substance to be detected (e.g., the hydrogen concentration, etc.). The distance between the fixed electrode member 51M and the movable electrode member 11M is changed thereby. The electrical capacitance between the fixed electrode member 51M and the movable electrode member 11M changes according to the change of the distance. The concentration of the substance to be detected, etc., can be detected by detecting the change of the electrical capacitance. The first sensor part 10A is, for example, an electrical capacitance-type sensor.

The change rate of the electrical capacitance with respect to the change of the concentration of the substance to be detected is high when the distance between the fixed electrode member 51M and the movable electrode member 11M is short. According to the embodiment, the first movable surface 11f is convex. The third distance d3 is less than the first distance d1 and less than the second distance d2. Thereby, the third distance d3 can be short at the central portion of the movable electrode member 11M. The change rate of the electrical capacitance can be increased thereby.

For example, there is a reference example in which the movable electrode member 11M is flat. In the reference example, the third distance d3 is equal to the first distance d1 and equal to the second distance d2. In such a reference example, when the distance between the fixed electrode member 51M and the movable electrode member 11M is reduced, the requirements on the fluctuation of the manufacturing processes, etc., are stringent.

According to the embodiment, the third distance d3 is short at the central portion of the movable electrode member 11M; and the first distance d1 and the second distance d2 around the central portion are not short. The change rate of the electrical capacitance can be increased thereby, and the requirements on the fluctuation of the manufacturing processes, etc., can still be relaxed.

According to the embodiment, for example, by adjusting the stress generated in the movable electrode member 11M, etc., the first movable surface 11f can be convex; and the third distance d3 can be less than the first distance d1 and less than the second distance d2.

As in the reference example described above, etc., generally, a technical idea is employed in which the stress of the movable electrode member 11M is suppressed, and the movable electrode member 11M is set to be flat. Instead of such a technical idea, according to the embodiment, a technical idea is employed in which the first movable surface 11f is set to be convex. Thereby, the change rate of the electrical capacitance can be increased while making the manufacturing easy. High detection sensitivity is obtained.

In the example as shown in FIG. 1B, the movable electrode member 11M includes a first insulating part 11i and a second insulating part 11j. The first insulating part 11i is between the fixed electrode member 51M and the second insulating part 11j. A movable electrode 11 is between the first insulating part 11i and the second insulating part 11j.

In the example, the length (the thickness) along the Z-axis direction of the first insulating part 11i is different from the length (the thickness) along the Z-axis direction of the second insulating part 11j. For example, the length (the thickness) along the Z-axis direction of the first insulating part 11i is less than the length (the thickness) along the Z-axis direction of the second insulating part 11j. Stress may be generated in the movable electrode member 11M by such thickness differences; and the first movable surface 11f may be convex due to the stress.

The first movable surface 11f may be set to be convex by the material of the first insulating part 11i being different from the material of the second insulating part 11j. The first movable surface 11f may be set to be convex by the formation conditions (e.g., the film formation conditions) of the first insulating part 11i being different from the formation conditions (e.g., the film formation conditions) of the second insulating part 11j.

According to the embodiment, the movable electrode 11 may include multiple stacked conductive films. The first movable surface 11f may be set to be convex by the characteristics of the multiple conductive films being different from each other.

The difference between the third distance d3 and the first distance d1 corresponds to the warp amount. According to the embodiment, the difference between the third distance d3 and the first distance d1 is not less than 0.1 times a thickness 11t along the first direction (the Z-axis direction) of the third movable portion 11c (referring to FIG. 1B). The change rate of the electrical capacitance can be effectively increased by such a warp amount. The difference between the third distance d3 and the first distance d1 may be not less than 0.5 times the thickness 11t along the first direction of the third movable portion 11c. The change rate of the electrical capacitance can be effectively and stably increased.

As described above, the distance between the fixed electrode member 51M and the movable electrode member 11M is changeable according to the concentration of a first element around the movable electrode member 11M. The first element is the element of a substance to be detected. The first element is, for example, hydrogen.

For example, at least a portion of the first support member 21 is deformable according to the concentration of the first element around the first support member 21. At least a portion of the second support member 22 is deformable according to the concentration of the first element around the second support member 22. For example, the first support member 21 and the second support member 22 deform due to the first element (the hydrogen to be detected, etc.) adhering to the first and second support members 21 and 22. For example, the volumes of the first and second support members 21 and 22 change according to the concentration of the first element. At least a portion of the first support member 21 and at least a portion of the second support member 22 are deformed thereby. According to the deformation, the distance between the fixed electrode member 51M and the movable electrode member 11M changes, and the electrical capacitance changes.

For example, the first element may adsorb to at least portions of the first and second support members 21 and 22. At least portions of the first and second support members 21 and 22 may store the first element.

For example, as shown in FIGS. 1A and 1B, the first support member 21 includes a functional film (a first functional film 21s). The second support member 22 includes a functional film (a second functional film 22s). The functional films (the first functional film 21s and the second functional film 22s) include, for example, a second element and a third element. The second element includes, for example, at least one selected from the group consisting of Pd and Pt. The third element includes, for example, Si. The functional films (the first functional film 21s and the second functional film 22s) include, for example, Pd and Si. Hydrogen (an example of the first element) efficiently adsorbs to the functional films. An efficient volume change is obtained.

The functional films (the first functional film 21s and the second functional film 22s) may further include, for example, a fourth element. The fourth element includes Cu. The functional films (the first functional film 21s and the second functional film 22s) include, for example, PdCuSi. For example, hydrogen (an example of the first element) efficiently adsorbs to PdCuSi. An efficient volume change is obtained.

In the example as shown in FIG. 1B, the first support member 21 includes a conductive layer 21p, a conductive layer 21q, an insulating layer 21i, an insulating layer 21j, and an insulating layer 21k. For example, the insulating layer 21j is between the insulating layer 21i and the first functional film 21s. The insulating layer 21k is between the insulating layer 21j and the first functional film 21s. The conductive layer 21p is between the insulating layer 21i and the insulating layer 21j. The conductive layer 21q is between the insulating layer 21j and the insulating layer 21k. For example, the movable electrode 11 is electrically connected with one of the conductive layer 21p or the conductive layer 21q and may be electrically drawn out externally. As described below, the first support member 21 may include a heater. The heater is electrically connected with the other of the conductive layer 21p or the conductive layer 21q and may be electrically drawn out externally.

In the example as shown in FIG. 1B, the second support member 22 includes a conductive layer 22p, a conductive layer 22q, an insulating layer 22i, an insulating layer 22j, and an insulating layer 22k. For example, the insulating layer 22j is between the insulating layer 22i and the second functional film 22s. The insulating layer 22k is between the insulating layer 22j and the second functional film 22s. The conductive layer 22p is between the insulating layer 22i and the insulating layer 22j. The conductive layer 22q is between the insulating layer 22j and the insulating layer 22k. For example, the movable electrode 11 is electrically connected with one of the conductive layer 22p or the conductive layer 22q and may be electrically drawn out externally. As described below, the second support member 22 may include a heater. The heater is electrically connected with the other of the conductive layer 22p or the conductive layer 22q and may be electrically drawn out externally.

As shown in FIG. 1A, the movable electrode member 11M may include a hole 11H.

Figure 2:
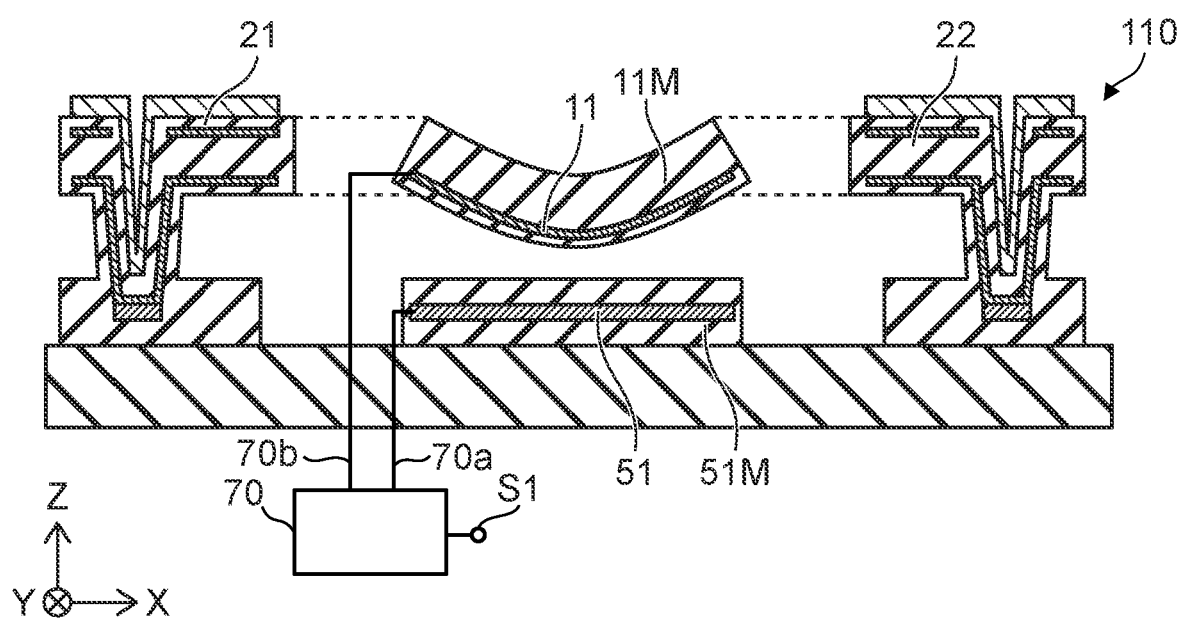
FIG. 2 is a schematic view illustrating the sensor according to the first embodiment.

FIG. 2 is a schematic view illustrating the sensor according to the first embodiment.

As shown in FIG. 2, the sensor 110 may include an electrical circuit 70. The electrical circuit 70 is electrically connected with the fixed electrode 51 and the movable electrode 11. For example, the electrical circuit 70 is electrically connected with the fixed electrode 51 via wiring 70a. For example, the electrical circuit 70 is electrically connected with the movable electrode 11 via wiring 70b. For example, the electrical circuit 70 may be electrically connected with the movable electrode 11 via a conductive layer (a conductive member) provided in at least one of the first support member 21 or the second support member 22. The wiring 70b may include a conductive layer provided in at least one of the first support member 21 or the second support member 22.

The electrical circuit 70 is configured to output a first signal S1. The first signal S1 corresponds to the electrical capacitance between the fixed electrode 51 and the movable electrode 11. As described above, the first signal S1 changes according to the change of the distance between the fixed electrode member 51M and the movable electrode member 11M. The first signal S1 changes according to the concentration of the first element around the first support member 21 and the second support member 22.

Figure 3A:
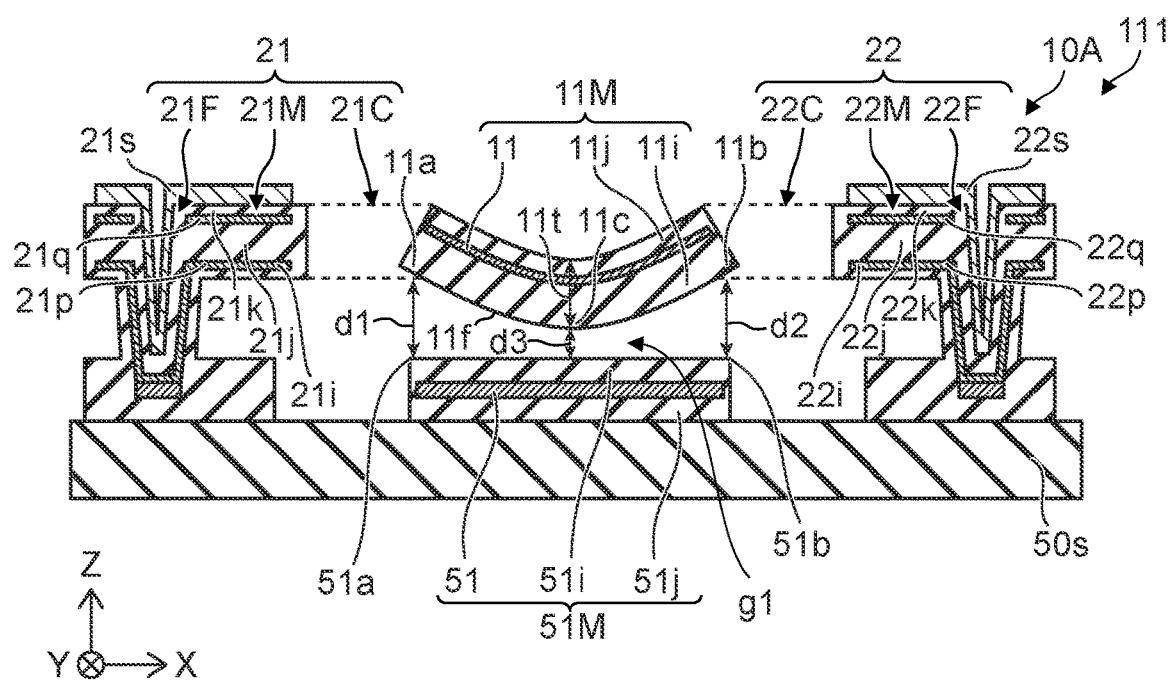
FIGS. 3A and 3B are schematic cross-sectional views illustrating a sensor according to the first embodiment.
Figure 3B:
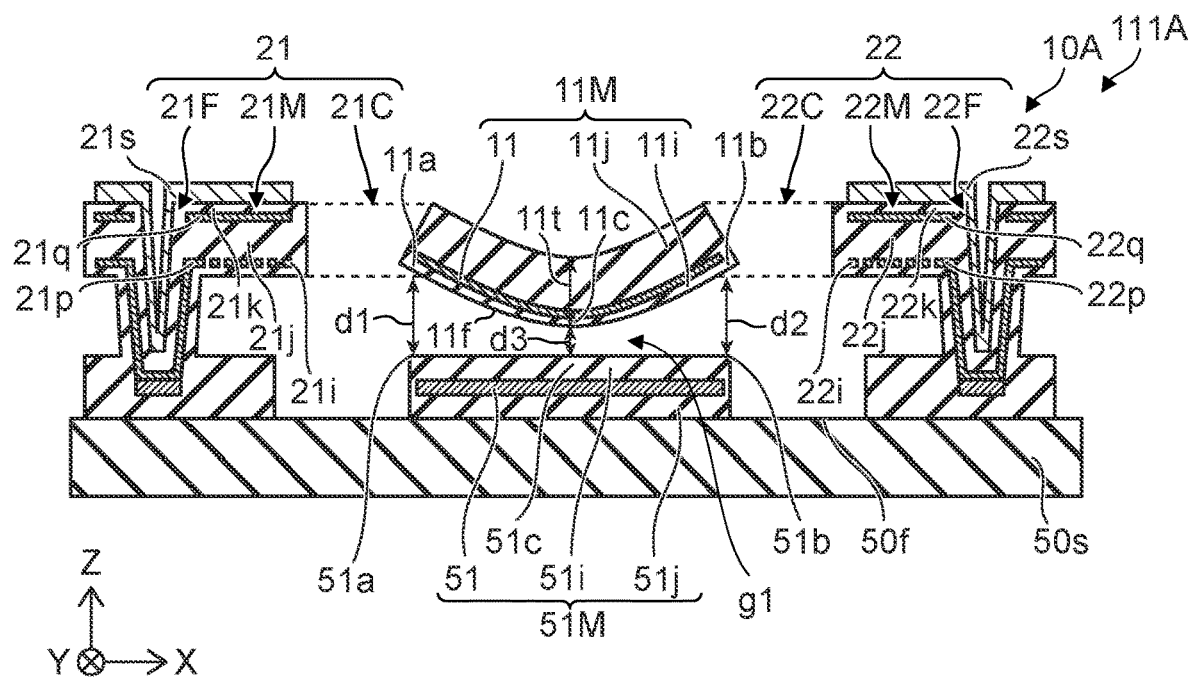

FIGS. 3A and 3B are schematic cross-sectional views illustrating a sensor according to the first embodiment.

These drawings are cross-sectional views corresponding to the line A1-A2 cross section of FIG. 1A. In the sensor 111 according to the embodiment as shown in FIG. 3A, the length (the thickness) along the Z-axis direction of the first insulating part 11i is greater than the length (the thickness) along the Z-axis direction of the second insulating part 11j. Stress may be generated in the movable electrode member 11M by such a thickness difference; and the first movable surface 11f may be set to be convex by the stress.

In the sensor 111 according to the embodiment as shown in FIG. 3B, the surface area in the X-Y plane of the conductive layer 21p may be different from the surface area in the X-Y plane of the conductive layer 21q. For example, the surface area in the X-Y plane of the conductive layer 21p is less than the surface area in the X-Y plane of the conductive layer 21q. The surface area in the X-Y plane of the conductive layer 22p may be different from the surface area in the X-Y plane of the conductive layer 22q. For example, the surface area in the X-Y plane of the conductive layer 22p is less than the surface area in the X-Y plane of the conductive layer 22q. For example, such surface area differences may be provided by at least one of the surface area or the number of holes provided in at least a portion of these conductive layers. Due to the surface area difference, at least one of the first intermediate support part 21M or the second intermediate support part 22M may be curved toward the base body 50s. For example, the distance between the fixed electrode member 51M and the movable electrode member 11M (which may be, for example, the third distance d3) is shorter. The conductive layer 21p and the conductive layer 22p may be, for example, heaters.

Figure 4A:
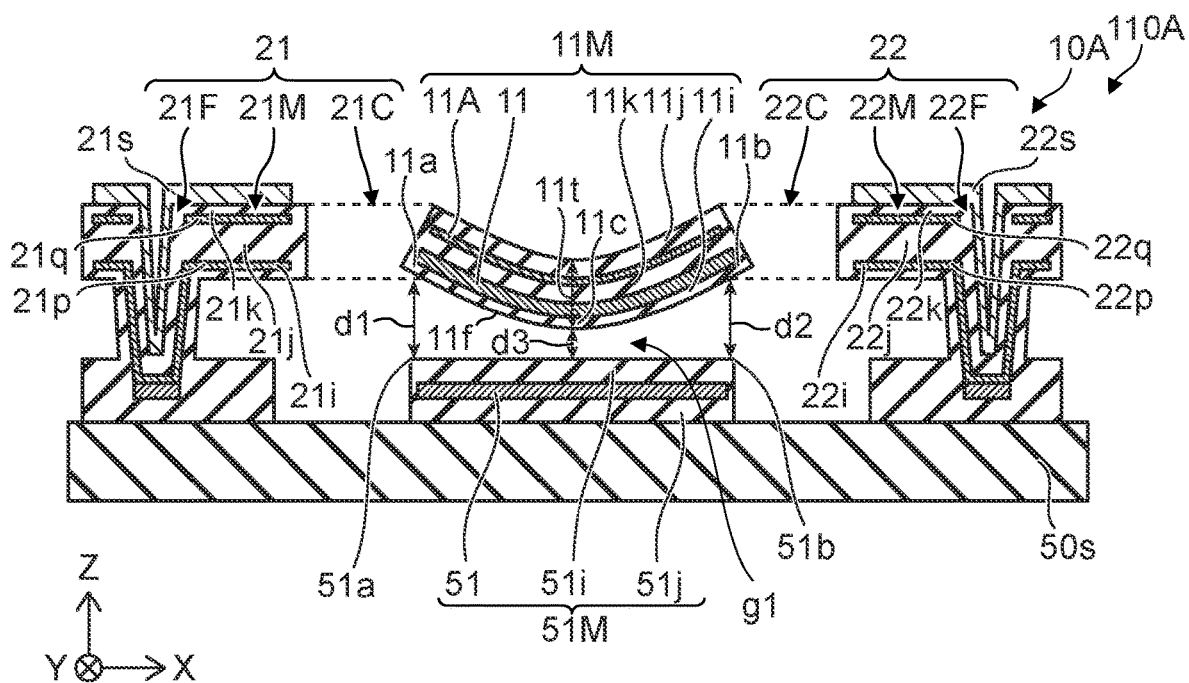
FIGS. 4A and 4B are schematic cross-sectional views illustrating sensors according to the first embodiment.
Figure 4B:
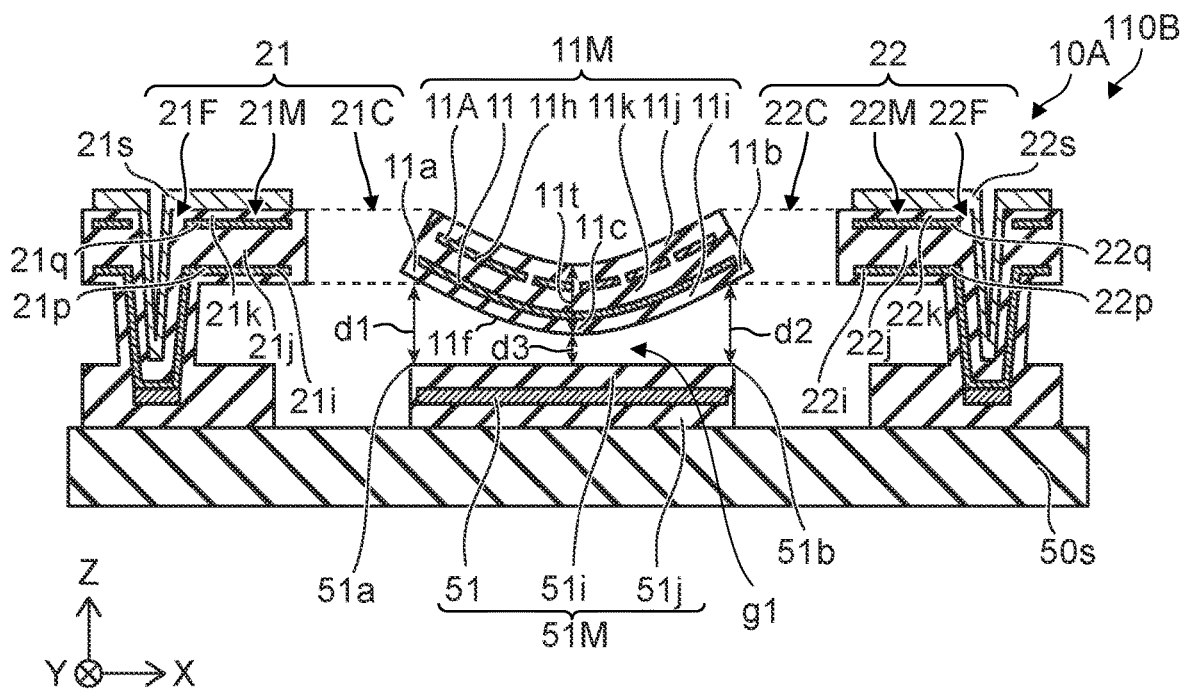

FIGS. 4A and 4B are schematic cross-sectional views illustrating sensors according to the first embodiment.

FIGS. 4A and 4B are cross-sectional views corresponding to the line A1-A2 cross section of FIG. 1A.

In a sensor 110A according to the embodiment as shown in FIG. 4A, the movable electrode 11 includes multiple stacked conductive films. For example, the movable electrode member 11M may be considered to include the movable electrode 11 and another movable electrode 11A. The direction from the movable electrode 11 toward the other movable electrode 11A is along the Z-axis direction. A third insulating part 11k is provided between the movable electrode 11 and the other movable electrode 11A.

In one example, the surface area of the movable electrode 11 and the surface area of the other movable electrode 11A are different from each other. In one example, the thickness of the movable electrode 11 and the thickness of the other movable electrode 11A are different from each other. For example, the movable electrode 11 and the other movable electrode 11A have mutually-different stress. The first movable surface 11f is convex.

As shown in FIG. 4B, in a sensor 110B according to the embodiment as well, for example, the movable electrode member 11M includes the movable electrode 11 and the other movable electrode 11A. At least one of the movable electrode 11 or the other movable electrode 11A may include a hole 11h. Due to the surface area of the hole 11h, the surface area of the movable electrode 11 and the surface area of the other movable electrode 11A may be different from each other. The opening ratio (or the coverage) of these electrodes may be different from each other due to the hole 11h, etc. The first movable surface 11f is convex.

Figure 5:
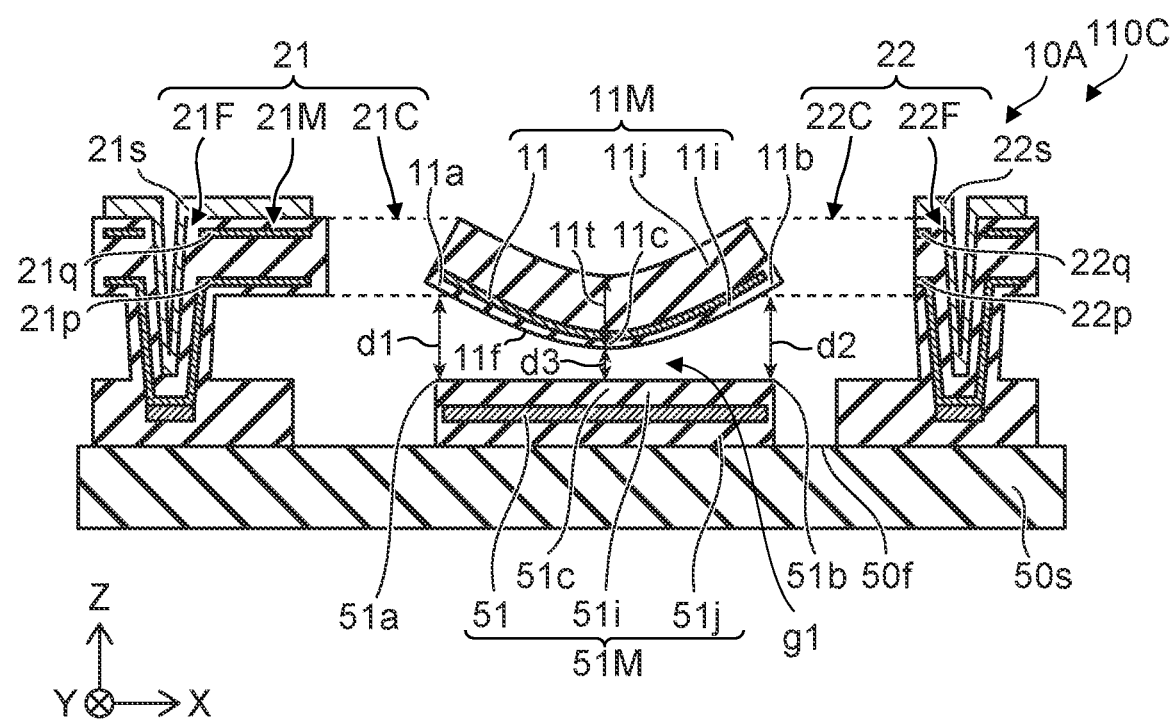
FIG. 5 is a schematic cross-sectional view illustrating a sensor according to the first embodiment.

FIG. 5 is a schematic cross-sectional view illustrating a sensor according to the first embodiment.

FIG. 5 is a cross-sectional view corresponding to the line A1-A2 cross section of FIG. 1A. The second intermediate support part 22M may be omitted as in the sensor 110C according to the embodiment shown in FIG. 5. In the sensors 110A to 110C as well, a sensor can be provided in which the detection sensitivity can be improved.

Figure 6:
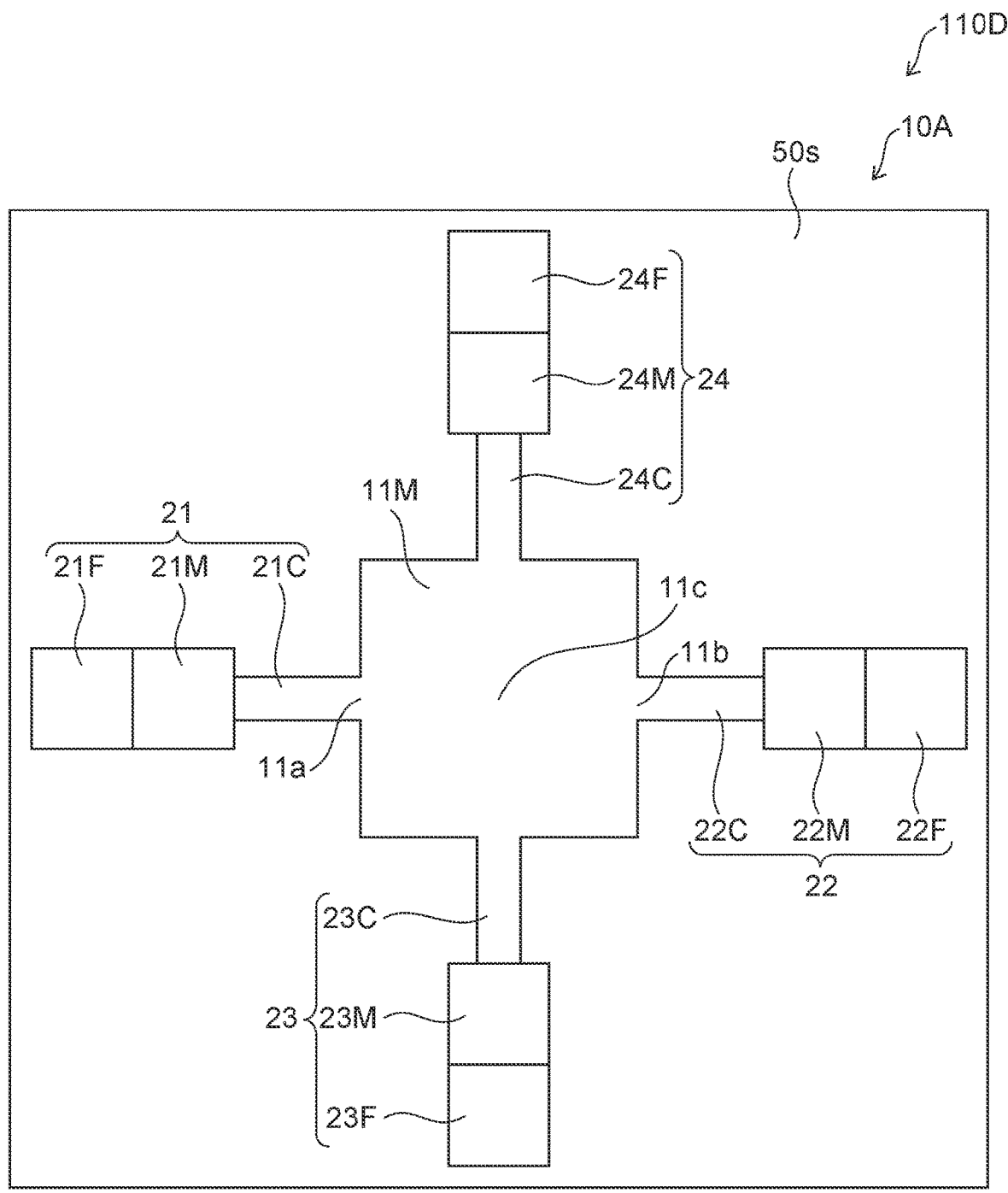
FIG. 6 is a schematic plan view illustrating sensors according to the first embodiment.
Figure 7:
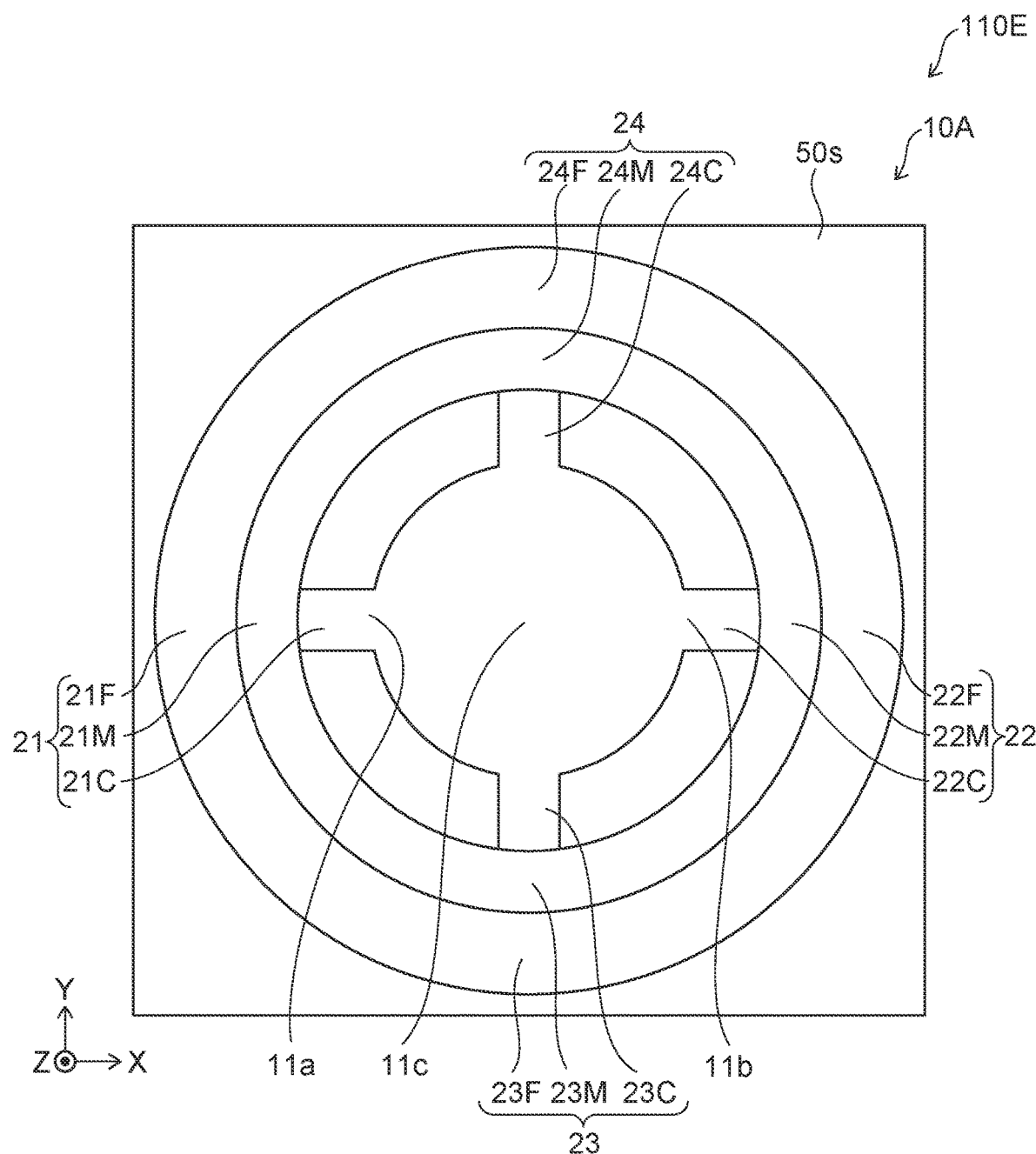
FIG. 7 is a schematic plan view illustrating sensors according to the first embodiment.

FIGS. 6 and 7 are schematic plan views illustrating sensors according to the first embodiment.

In sensors 110D and 110E according to the embodiment as shown in FIGS. 6 and 7, a third support member 23 and a fourth support member 24 are provided in addition to the first and second support members 21 and 22. The first to fourth support members 21 to 24 support the movable electrode member 11M to provide the first gap g1 between the fixed electrode member 51M and the movable electrode member 11M. For example, the direction from the first support member 21 toward the second support member 22 crosses the direction from the third support member 23 toward the fourth support member 24. For example, the third support member 23 includes a third fixed part 23F, a third intermediate support part 23M, and a third connection part 23C. For example, the fourth support member 24 includes a fourth fixed part 24F, a fourth intermediate support part 24M, and a fourth connection part 24C. The configurations of the third and fourth support members 23 and 24 may be similar to the configurations of the first and second support members 21 and 22.

As in the sensor 110E shown in FIG. 7, the first to fourth fixed parts 21F to 24F may be continuous with each other. In the sensors 110D and 110E as well, a sensor can be provided in which the detection sensitivity can be improved.

Figure 8A:
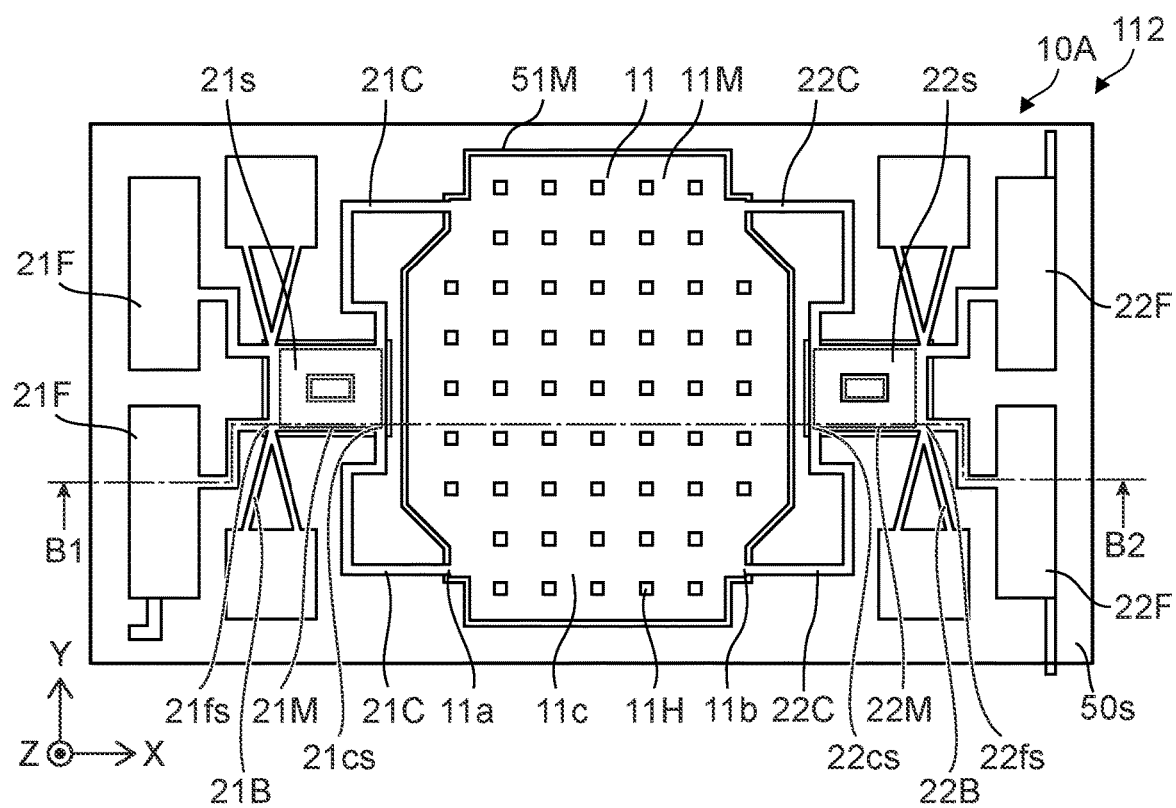
FIGS. 8A and 8B are schematic views illustrating a sensor according to the first embodiment.
Figure 8B:
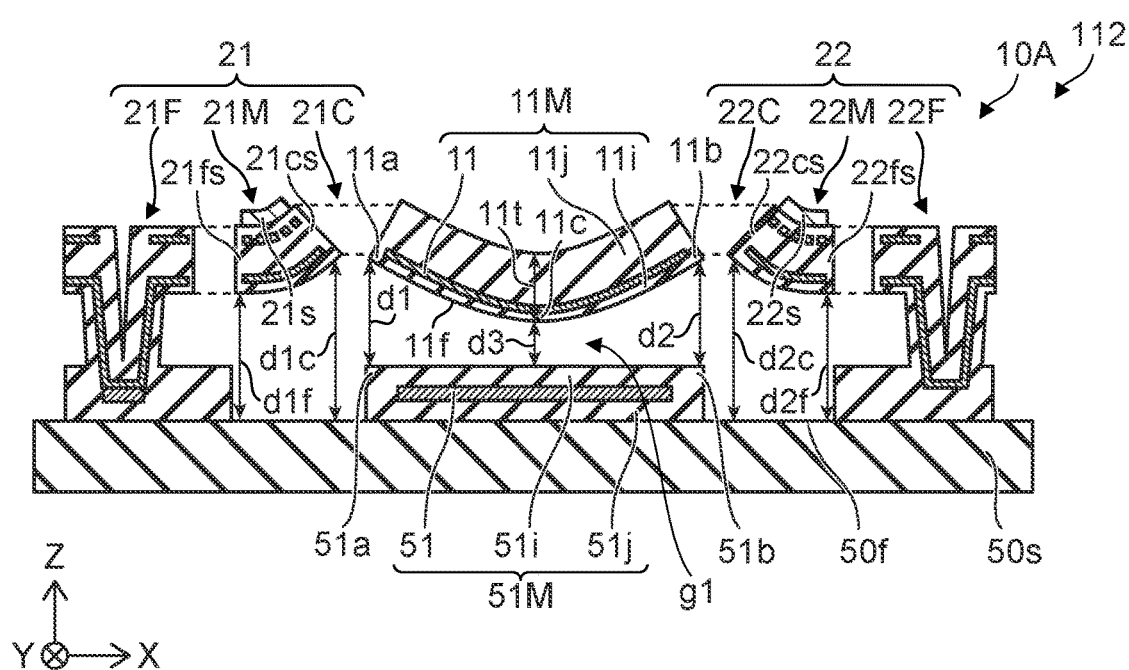

FIGS. 8A and 8B are schematic views illustrating a sensor according to the first embodiment.

FIG. 8A is a plan view. FIG. 8B is a line B1-B2 cross-sectional view of FIG. 8A.

As shown in FIGS. 8A and 8B, the sensor 112 according to the embodiment also includes the base body 50s and the first sensor part 10A. In the example as well, the first sensor part 10A includes the fixed electrode member 51M, the movable electrode member 11M, the first support member 21, and the second support member 22. In the sensor 112 as shown in FIG. 8B, the first support member 21 and the second support member 22 are curved.

In the sensor 112 as shown in FIG. 8B, the first intermediate support part 21M of the first support member 21 includes a first fixed part-side portion 21fs and a first connection part-side portion 21cs. The first fixed part-side portion 21fs is connected with the first fixed part 21F. The first connection part-side portion 21cs is connected with the first connection part 21C.

As shown in FIG. 8B, the height of the first fixed part-side portion 21fs is different from the height of the first connection part-side portion 21cs when referenced to the base body 50s. A distance d1c along the first direction (the Z-axis direction) between the base body 50s and the first connection part-side portion 21cs is greater than a distance d1f along the first direction between the base body 50s and the first fixed part-side portion 21fs.

In the sensor 112 as shown in FIG. 8B, the second intermediate support part 22M of the second support member 22 includes a second fixed part-side portion 22fs and a second connection part-side portion 22cs. The second fixed part-side portion 22fs is connected with the second fixed part 22F. The second connection part-side portion 22cs is connected with the second connection part 22C.

As shown in FIG. 8B, a distance d2c along the first direction (the Z-axis direction) between the base body 50s and the second connection part-side portion 22cs is greater than a distance d2f along the first direction between the base body 50s and the second fixed part-side portion 22fs.

By setting the heights of the first and second connection part-side portions 21cs and 22cs to be high, for example, the first movable surface 11f easily may be convex. The change rate of the electrical capacitance is easily increased.

As described below, the first support member 21 and the second support member 22 may include a heater. The heater increases the temperature of the functional films (the first functional film 21s, the second functional film 22s, etc.). For example, the water that is adsorbed to the functional films is separated from the functional films; for example, the adsorption characteristics for the first element of the functional films are recovered. By setting the first connection part-side portion 21cs and the second connection part-side portion 22cs to be high, the distance between the first intermediate support part 21M and the base body 50s and the distance between the second intermediate support part 22M and the base body 50s can be long. For example, the temperature of the functional films can be efficiently increased thereby.

As shown in FIG. 8A, the length along the third direction (e.g., the Y-axis direction) of at least a portion of the first connection part 21C is less than the length along the third direction of the first intermediate support part 21M. For example, the length along the third direction of at least a portion of the second connection part 22C is less than the length along the third direction of the second intermediate support part 22M.

In the example as shown in FIG. 8A, the first fixed part-side portion 21fs is supported by a beam 21B. The second fixed part-side portion 22fs is supported by a beam 22B. The beam 21B and the beam 22B extend in the Y-axis direction. In the example, the first fixed part-side portion 21fs is between the two beams 21B. The second fixed part-side portion 22fs is between the two beams 22B. For example, the positions of the first and second fixed part-side portions 21fs and 22fs are stable.

Otherwise, the configuration described in reference to the sensor 110 is applicable to the configurations of the sensors 111 and 112.

Figure 9A:
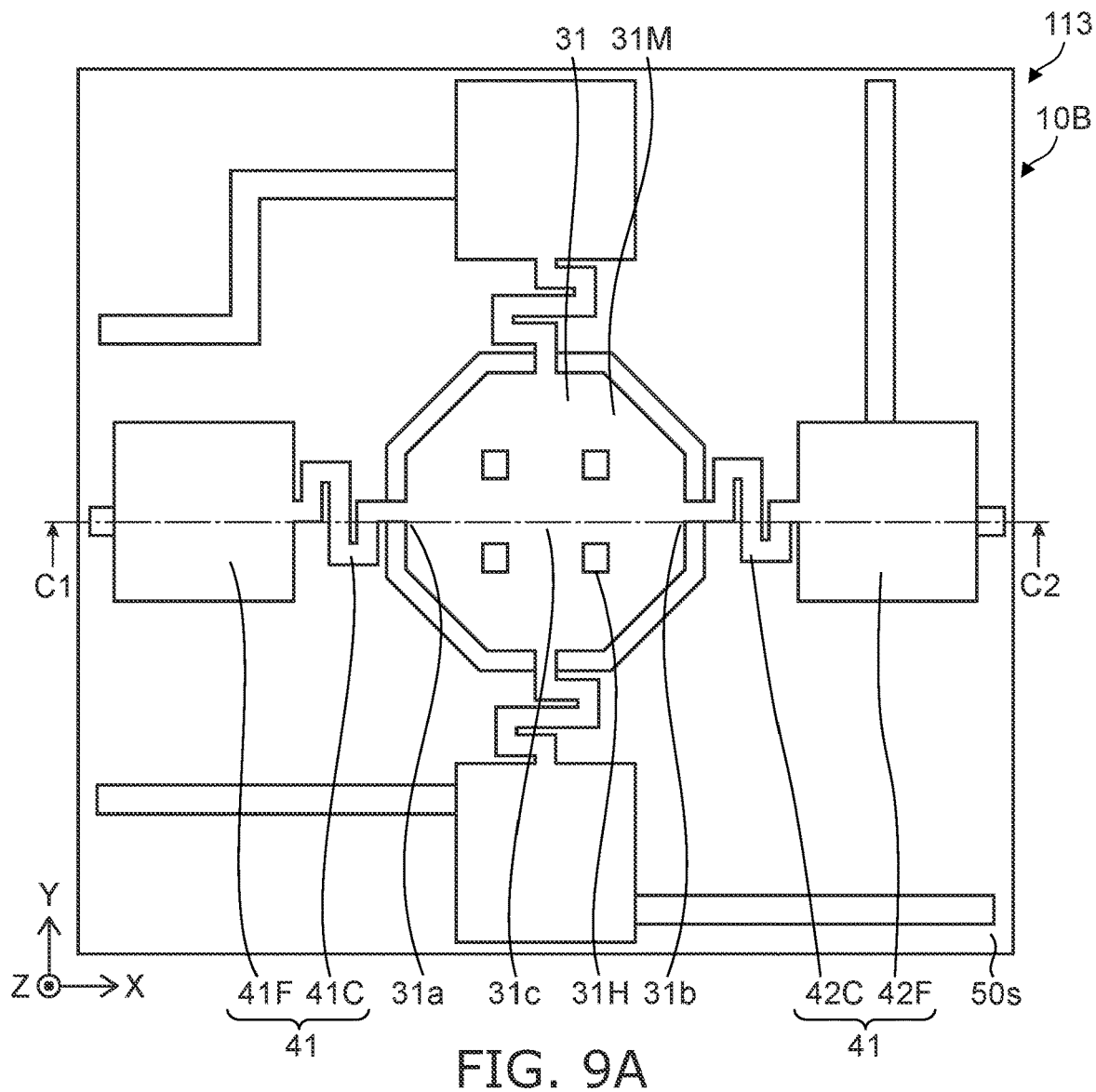
FIGS. 9A and 9B are schematic views illustrating a sensor according to the first embodiment.
Figure 9B:
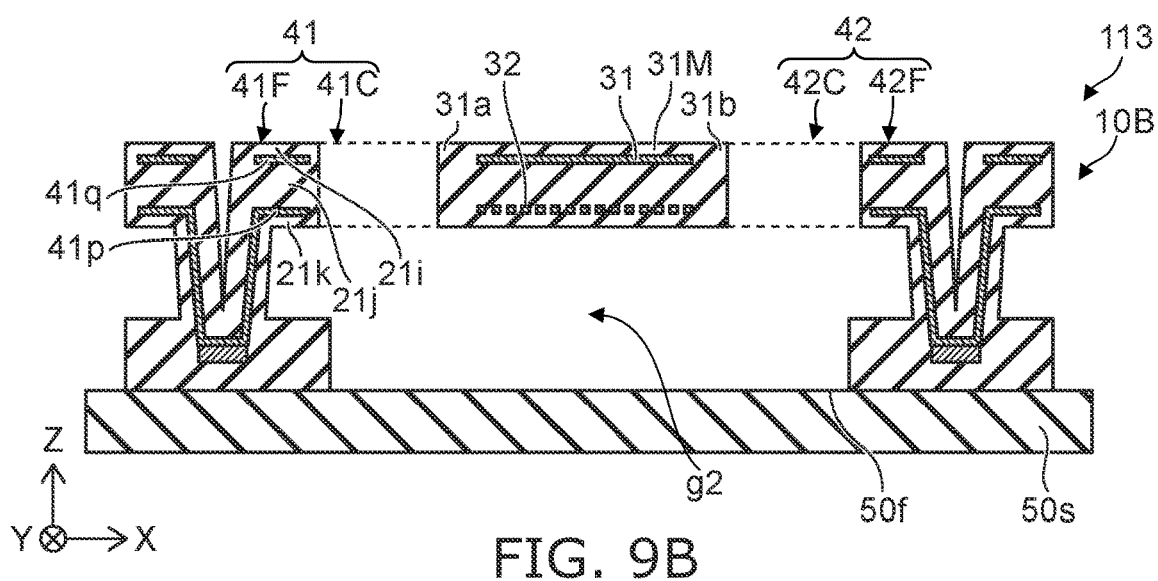

FIGS. 9A and 9B are schematic views illustrating a sensor according to the first embodiment.

FIG. 9A is a plan view. FIG. 9B is a line C1-C2 cross-sectional view of FIG. 9A.

The sensor 113 according to the embodiment may further include a second sensor part 10B in addition to the first sensor part 10A described above. The configurations described in reference to the sensors 110, 111, 111A, 112, and 110A to 110E are applicable to the first sensor part 10A of the sensor 113. An example of the second sensor part 10B will now be described.

As shown in FIGS. 9A and 9B, the second sensor part 10B includes a sensor member 31M, a first support part 41, and a second support part 42.

The sensor member 31M includes a first sensor portion 31a and a second sensor portion 31b. The sensor member 31M includes a conductive member (e.g., a first conductive member 31).

The first support part 41 is fixed to the base body 50s and connected with the first sensor portion 31a. The second support part 42 is fixed to the base body 50s and connected with the second sensor portion 31b. The first and second support parts 41 and 42 support the sensor member 31M to provide a second gap g2 between the base body 50s and the sensor member 31M.

The electrical resistance of the conductive member (e.g., the first conductive member 31) changes due to the concentration of the substance to be detected around the sensor member 31M. For example, when the concentration is high, the heat of the conductive member is easily scattered via the substance to be detected. The electrical resistance of the conductive member changes according to the temperature of the conductive member. Information that relates to the concentration of the substance to be detected is obtained by detecting the change of the electrical resistance of the conductive member. The second sensor part 10B is, for example, a thermal conduction-type electrical resistance-type sensor.

Generally, in a thermal conduction-type electrical resistance-type sensor, the substance to be detected can be detected with high accuracy in a relatively high region of the concentration of the substance (the element) to be detected. On the other hand, an electrical capacitance-type sensor can detect the substance to be detected with high accuracy in a low region of the concentration of the substance to be detected. By combining the first sensor part 10A and the second sensor part 10B, the concentration can be detected with high accuracy in a wide concentration range. A detection in a wide dynamic range is possible. In the second sensor part 10B, the substance to be detected may be the first element (e.g., hydrogen, etc.) or another substance (e.g., carbon dioxide, etc.). For example, by providing the first sensor part 10A and the second sensor part 10B, the first element and a substance that is different from the first element can be detected.

As shown in FIG. 9B, the sensor member 31M may further include a heater 32. The temperature of the sensor member 31M is increased by the heater 32. For example, information that relates to the concentration of the element to be detected is obtained from the degree of the change of the resistance of the first conductive member 31 with respect to the electrical power supplied to the heater 32.

As shown in FIGS. 9A and 9B, the first support part 41 includes a first support fixed part 41F and a first support connection part 41C. The first support fixed part 41F is fixed to the base body 50s. One end of the first support connection part 41C is supported by the first support fixed part 41F. The first support connection part 41C supports the sensor member 31M. The second support part 42 includes a second support fixed part 42F and a second support connection part 42C. The second support fixed part 42F is fixed to the base body 50s. One end of the second support connection part 42C is supported by the second support fixed part 42F. The second support connection part 42C supports the sensor member 31M. The first support connection part 41C and the second support connection part 42C are, for example, spring parts.

Figure 10:
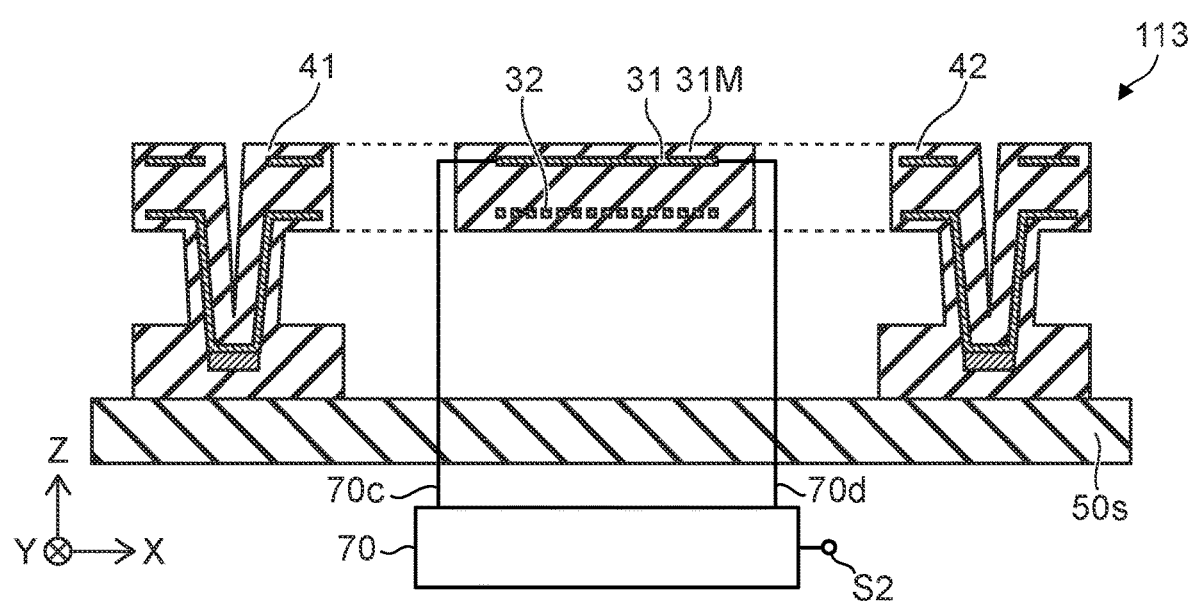
FIG. 10 is a schematic view illustrating the sensor according to the first embodiment.

FIG. 10 is a schematic view illustrating the sensor according to the first embodiment.

As shown in FIG. 10, the sensor 113 may include the electrical circuit 70. The electrical circuit 70 is electrically connected with the conductive member (e.g., the first conductive member 31) included in the sensor member 31M. For example, the electrical circuit 70 is electrically connected with one end of the first conductive member 31 via wiring 70c. For example, the electrical circuit 70 is electrically connected with another end of the first conductive member 31 via wiring 70d.

The electrical circuit 70 is configured to output a second signal S2. The second signal S2 corresponds to the electrical resistance of a conductive member (the first conductive member 31). As described above, the electrical resistance of the conductive member (the first conductive member 31) changes according to the concentration of the substance (the first element) to be detected around the sensor member 31M.

In the sensor 113, the electrical circuit 70 may output at least one of the first signal S1 (referring to FIG. 2) or the second signal S2. The electrical circuit 70 may output a signal derived from the first and second signals S1 and S2. A detection signal in a wide dynamic range is obtained.

Figure 11A:
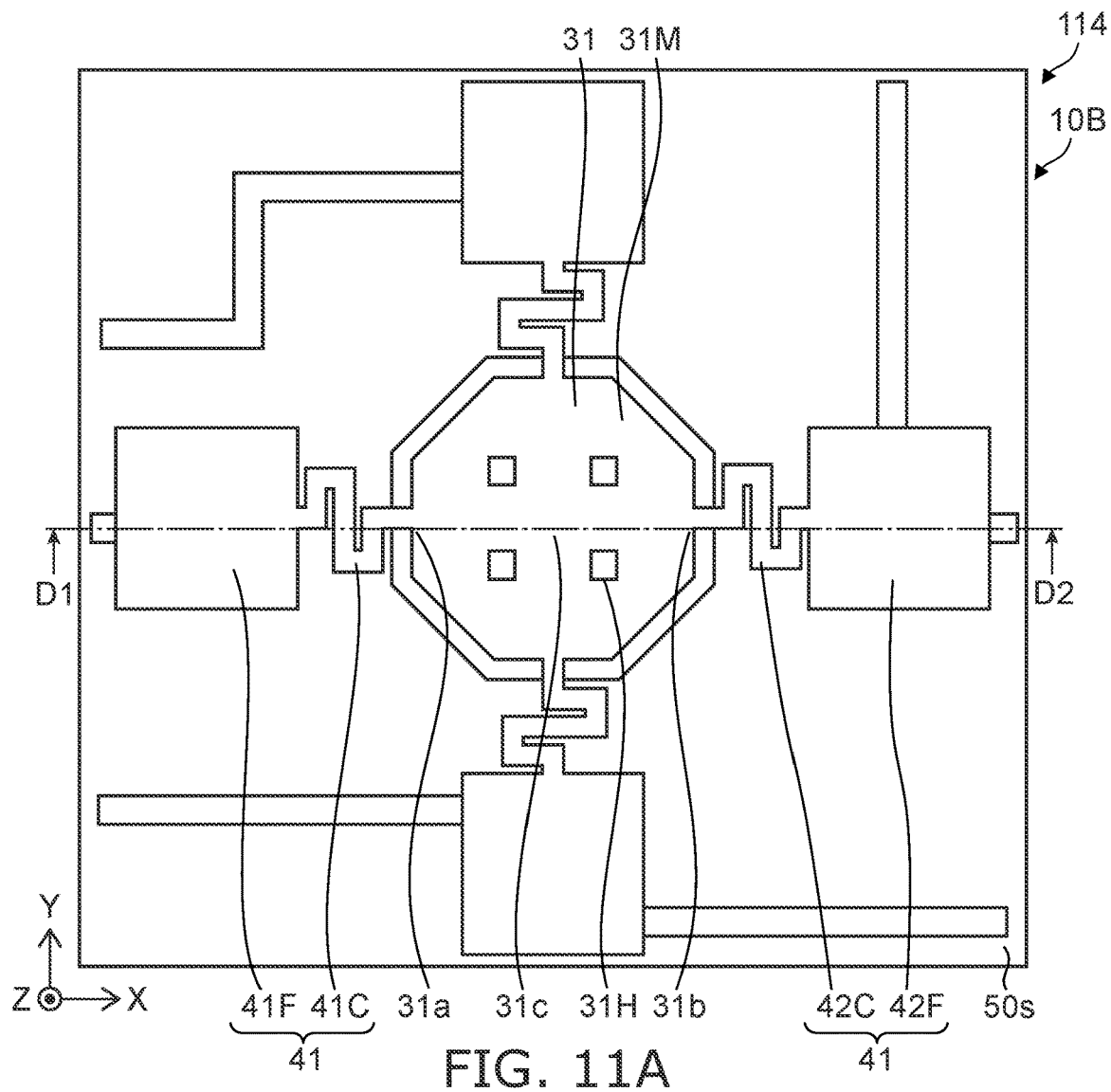
FIGS. 11A and 11B are schematic views illustrating a sensor according to the first embodiment.
Figure 11B:
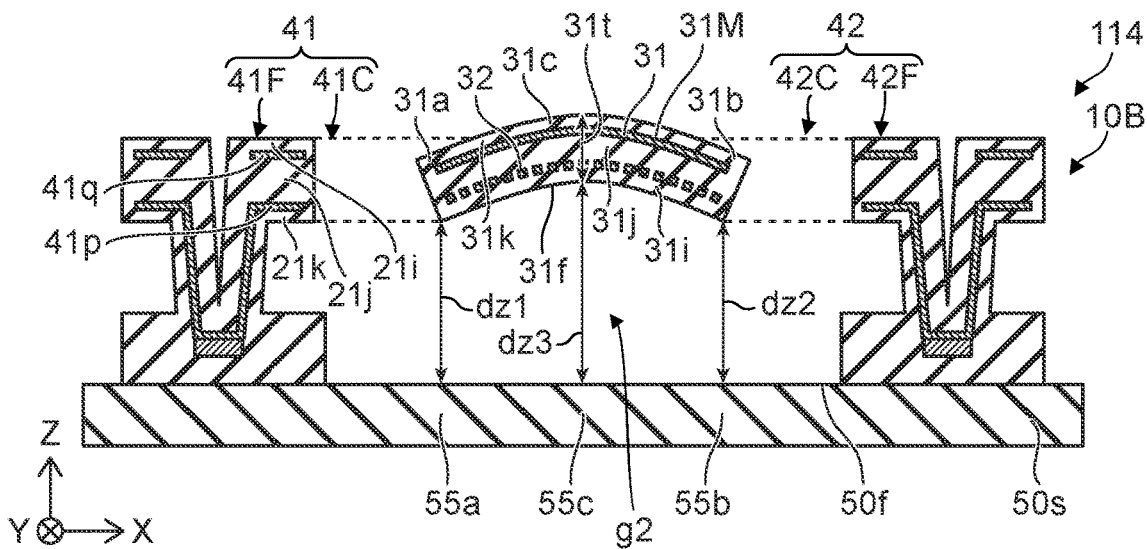

FIGS. 11A and 11B are schematic views illustrating a sensor according to the first embodiment.

FIG. 11A is a plan view. FIG. 11B is a line D1-D2 cross-sectional view of FIG. 11A.

In the sensor 114 as shown in FIGS. 11A and 11B, the sensor member 31M may be curved. For example, the sensor member 31M includes a base body counter surface $31f$. The base body counter surface $31f$ faces the base body 50s. The base body counter surface $31f$ is concave.

For example, the sensor member 31M includes a third sensor portion 31c in addition to the first sensor portion 31a and the second sensor portion 31b. The third sensor portion 31c is between the first sensor portion 31a and the second sensor portion 31b.

As shown in FIG. 11B, the base body 50s includes a first counter portion 50a, a second counter portion 50b, and a third counter portion 50c. The first counter portion 50a faces the first sensor portion 31a. The second counter portion 50b faces the second sensor portion 31b. The third counter portion 50c faces the third sensor portion 31c.

The distance along the first direction (the Z-axis direction) between the first counter portion 50a and the first sensor portion 31a is taken as a first counter distance dz1. The distance along the first direction (the Z-axis direction) between the second counter portion 50b and the second sensor portion 31b is taken as a second counter distance dz2. The distance along the first direction (the Z-axis direction) between the third counter portion 50c and the third sensor portion 31c is taken as a third counter distance dz3. In the sensor 114, the third counter distance dz3 is greater than the first counter distance dz1. The third counter distance dz3 is greater than the second counter distance dz2.

Thus, because the base body counter surface $31f$ is concave, and because the third counter distance dz3 is greater than the first counter distance dz1 and greater than the second counter distance dz2, for example, the distance between the base body 50s and the central portion of the sensor member 31M can be long.

As described above, for example, the electrical resistance of the sensor member 31M changes according to the concentration of the substance to be detected. When the distance between the base body 50s and the central portion of the sensor member 31M is excessively short, the heat from the sensor member 31M is easily conducted to the base body 50s, etc. Therefore, it is difficult to increase the change rate of the electric conduction with respect to the change of the concentration of the substance to be detected. Conversely, when the distance between the base body 50s and the central portion of the sensor member 31M is long, the conduction of the heat from the sensor member 31M to the base body 50s, etc., can be suppressed. The change rate of the electric conduction with respect to the change of the concentration of the element to be detected can be increased thereby.

According to the embodiment, for example, the first sensor part 10A and the second sensor part 10B are provided in one base body 50s. In such a case, high productivity is obtained because the movable electrode member 11M of the first sensor part 10A and the sensor member 31M of the second sensor part 10B are formed in the same manufacturing process. For example, the thickness of the sacrificial layer located between the base body 50s and the movable electrode member 11M and the thickness of the sacrificial layer located between the base body 50s and the sensor member 31M are substantially the same.

According to the embodiment, for example, the lower surface (the first movable surface 11f) of the movable electrode member 11M is convex toward the base body 50s; and the lower surface (the base body counter surface 31f) of the sensor member 31M is concave toward the base body 50s. Thereby, the distance (the third distance d3) between the base body 50s and the central portion of the movable electrode member 11M is short; and the distance (the third counter distance dz3) between the base body 50s and the central portion of the sensor member 31M is long. Such a length difference is obtained by using sacrificial layers having the same thickness. High sensitivity in the detection of the electrical capacitance and high sensitivity in the detection of the electrical resistance are obtained thereby. According to the embodiment, detection with high sensitivity in a wide dynamic range is possible.

For example, the difference between the third counter distance dz3 and the first counter distance dz1 is not less than 0.1 times the thickness along the first direction (the Z-axis direction) of the third sensor portion 31c. The difference between the third counter distance dz3 and the first counter distance dz1 may be not less than 0.5 times the thickness along the first direction (the Z-axis direction) of the third sensor portion 31c.

Figure 12:
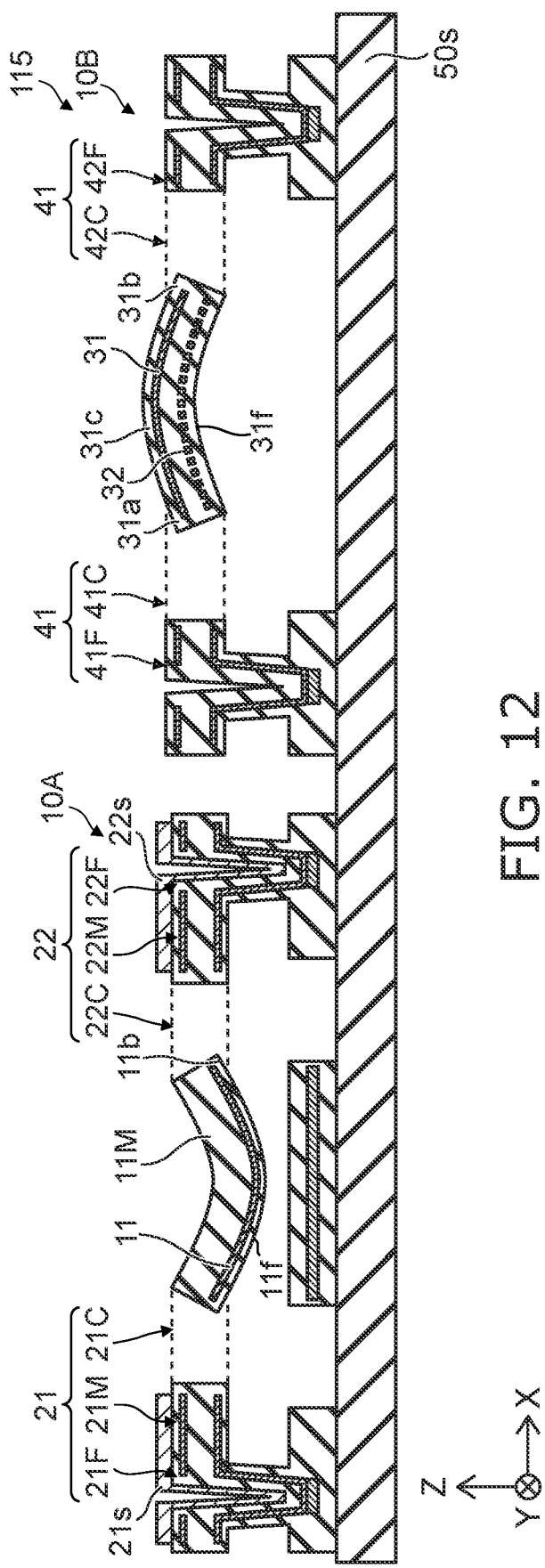
FIG. 12 is a schematic cross-sectional view illustrating a sensor according to the first embodiment.

FIG. 12 is a schematic cross-sectional view illustrating a sensor according to the first embodiment.

As shown in FIG. 12, the configuration of the first sensor part 10A described in reference to the sensor 110 is applied to the first sensor part 10A of the sensor 115 according to the embodiment. The configuration of the second sensor part 10B described in reference to the sensor 114 is applied to the second sensor part 10B of the sensor 115. As shown in FIG. 12, the first movable surface 11f is convex; and the base body counter surface 31f is concave.

Figure 13:
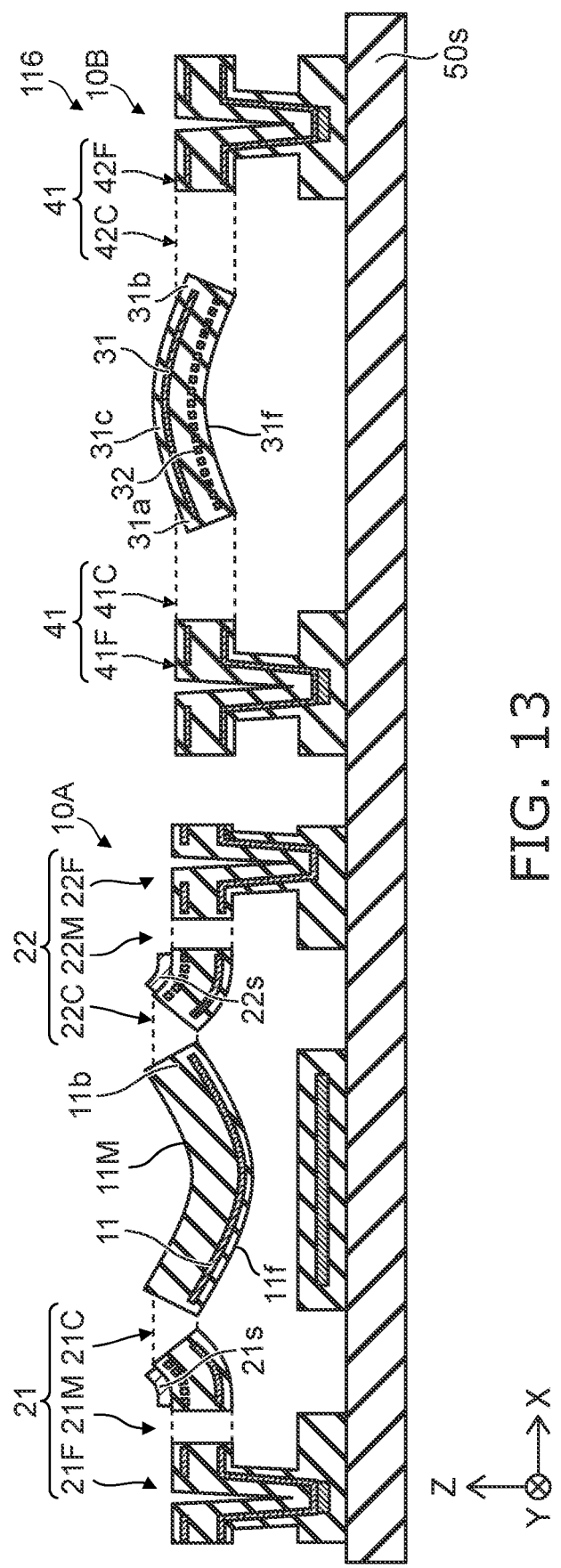
FIG. 13 is a schematic cross-sectional view illustrating a sensor according to the first embodiment.

FIG. 13 is a schematic cross-sectional view illustrating a sensor according to the first embodiment.

As shown in FIG. 13, the configuration of the first sensor part 10A described in reference to the sensor 112 is applied to the first sensor part 10A of the sensor 116 according to the embodiment. The configuration of the second sensor part 10B described in reference to the sensor 114 is applied to the second sensor part 10B of the sensor 116. As shown in FIG. 13, the first movable surface 11f is convex; and the base body counter surface 31f is concave. As shown in FIG. 13, the first connection part 21C and the second connection part 22C are warped to be curved upward.

Figure 14:
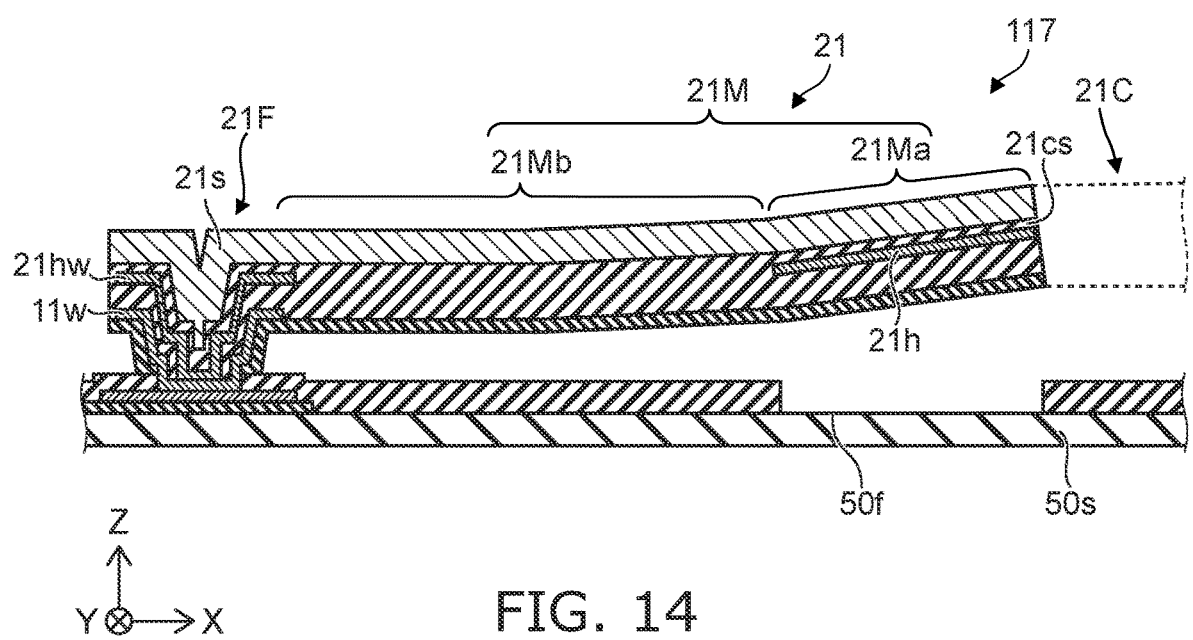
FIG. 14 is a schematic cross-sectional view illustrating a sensor according to the first embodiment.

FIG. 14 is a schematic cross-sectional view illustrating a sensor according to the first embodiment.

FIG. 14 illustrates a portion of the sensor 117 according to the embodiment. In the sensor 117, the first support member 21 includes the first fixed part 21F, the first intermediate support part 21M, and the first connection part 21C. A heater 21h is provided in a portion of the first intermediate support part 21M. The first intermediate support part 21M includes a first intermediate region 21Ma and a second intermediate region 21Mb. The first intermediate region 21Ma includes the heater 21h. The second intermediate region 21Mb does not include the heater 21h. The first intermediate region 21Ma is connected with the first connection part 21C. The second intermediate region 21Mb is between the first fixed part 21F and the first intermediate region 21Ma. By providing the second intermediate region 21Mb, the heat due to the heater 21h of the first intermediate region 21Ma is not easily scattered. The thermal resistance can be increased by the second intermediate region 21Mb. The temperature can be effectively increased by the heater 21h. For example, the first functional film 21s can be effectively heated. For example, various elements that are included in the first functional film 21s are easily removed effectively.

For example, the amount of the warp of the first intermediate support part 21M is easily increased by providing the first intermediate region 21Ma and the second intermediate region 21Mb in the first intermediate support part 21M.

As shown in FIG. 14, the first fixed part 21F may include wiring 21hw that is electrically connected with the heater 21h. The first fixed part 21F may include wiring 11w that is electrically connected with the movable electrode 11 (referring to FIG. 1B, etc.)

A configuration of the first support member 21 such as that described above is applicable to the second support member 22.

According to the first embodiment, the first movable surface 11f may be substantially flat; and the first support member 21 may have the configuration described in reference to FIG. 8B. For example, the first support member 21 that is fixed to the base body 50s and connected with the first movable portion 11a is provided, and the second support member 22 that is fixed to the base body 50s and connected with the second movable portion 11b is provided. The first support member 21 includes the first fixed part-side portion 21fs and the first connection part-side portion 21cs. The first connection part-side portion 21cs is between the first fixed part-side portion 21fs and the first movable portion 11a. The second support member 22 includes the second fixed part-side portion 22fs and the second connection part-side portion 22cs. The second connection part-side portion 22cs is between the second fixed part-side portion 22fs and the second movable portion 11b. As shown in FIG. 8B, for example, the distance d1c along the first direction (the Z-axis direction) between the base body 50s and the first connection part-side portion 21cs may be greater than the distance d1f along the first direction between the base body 50s and the first fixed part-side portion 21fs. For example, the distance d2c along the first direction (the Z-axis direction) between the base body 50s and the second connection part-side portion 22cs may be greater than the distance d2f along the first direction between the base body 50s and the second fixed part-side portion 22fs. For example, the difference between the distance d1c and the distance d1f may be not less than 0.1 times the length (the thickness) along the first direction of the first connection part-side portion 21cs. For example, the difference may be not less than 0.5 times the length (the thickness) along the first direction of the first connection part-side portion 21cs. In such an example, the direction from the first fixed part 21F toward the movable electrode member 11M is along the second direction (e.g., the X-axis direction) crossing the first direction (the Z-axis direction). The length along the third direction (the Y-axis direction) of at least a portion of the first connection part 21C is less than the length along the third direction of the first intermediate support part 21M. The third direction crosses a plane including the first and second directions.

According to the embodiment, the second sensor part 10B may be provided without providing the first sensor part 10A. In such a case, the sensor (e.g., the sensor 113 illustrated in FIG. 9B) includes the base body 50s and the sensor part (e.g., the second sensor part 10B). The sensor part (the second sensor part 10B) includes the sensor member 31M, the first support part 41, and the second support part 42 (referring to FIG. 9B). The sensor member 31M includes the first sensor portion 31a, the second sensor portion 31b, and the third sensor portion 31c between the first sensor portion 31a and the second sensor portion 31b. The first support part 41 is fixed to the base body 50s and connected with the first sensor portion 31a. The second support part 42 is fixed to the base body 50s and connected with the second sensor portion 31b. The first and second support parts 41 and 42 support the sensor member 31M to provide the second gap g2 between the base body 50s and the sensor member 31M (referring to FIG. 9B).

As shown in FIG. 9B, the base body 50s includes the first counter portion 50a facing the first sensor portion 31a, the second counter portion 50b facing the second sensor portion 31b, and the third counter portion 50c facing the third sensor portion 31c. The third counter distance dz3 along the first direction (the Z-axis direction) between the third counter portion 50c and the third sensor portion 31c may be greater than the first counter distance dz1 along the first direction between the first counter portion 50a and the first sensor portion 31a and greater than the second counter distance dz2 along the first direction between the second counter portion 50b and the second sensor portion 31b (referring to FIG. 9B).

Figure 15A:
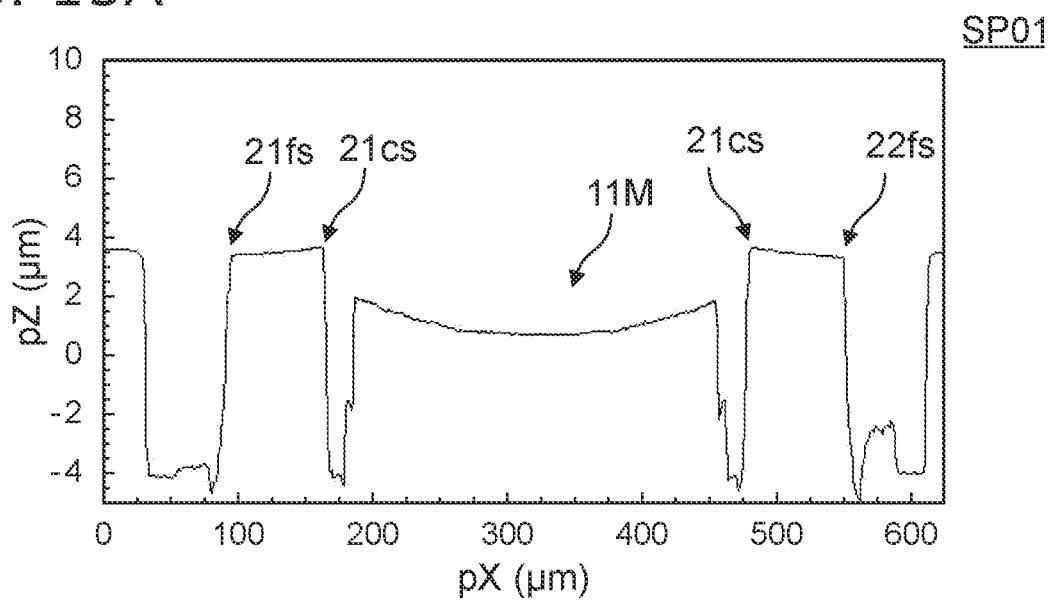
FIGS. 15A and 15B are schematic views illustrating characteristics of the sensor.
Figure 15B:
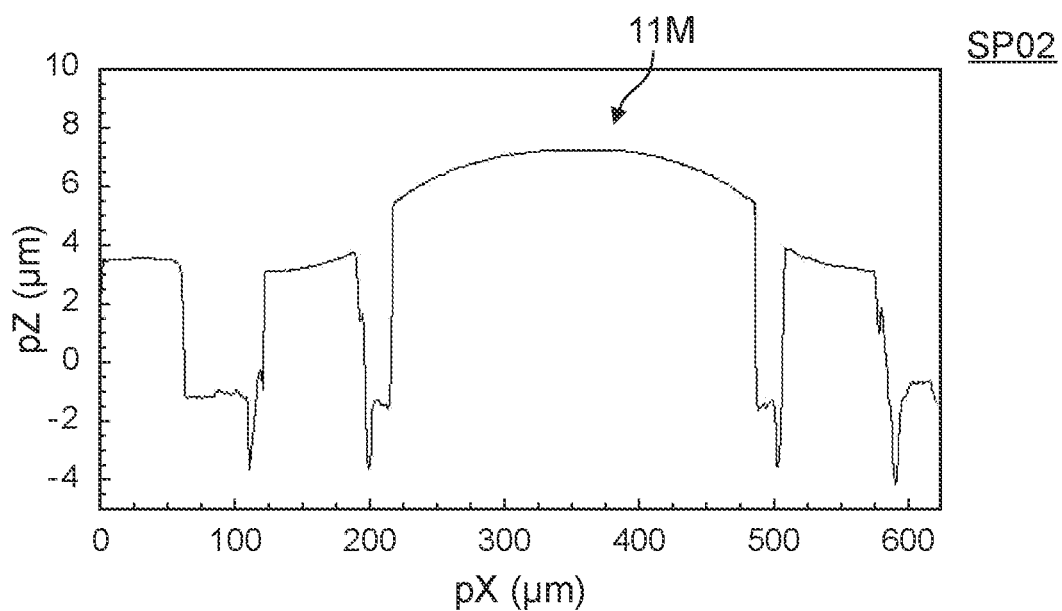

FIGS. 15A and 15B are schematic views illustrating characteristics of the sensor.

These figures illustrate measurement results of the unevenness (the height in the Z-axis direction) of the surface of the first sensor part 10A. FIG. 15A corresponds to a first sample SP01. FIG. 15B corresponds to a second sample SP02. The configurations of the layers of the first sample SP01 are different from the configurations of the layers of the second sample SP02. In these figures, the horizontal axis is a position pX in the X-axis direction. In these figures, the vertical axis is a position pZ (the height) in the Z-axis direction.

As shown in FIG. 15A, the movable electrode member 11M is warped to be convex downward in the first sample SP01. In the first sample SP01, the first connection part-side portion 21cs is higher than the first fixed part-side portion 21fs. The second connection part-side portion 22cs is higher than the second fixed part-side portion 22fs.

As shown in FIG. 15B, the movable electrode member 11M is warped to be convex upward in the second sample SP02. Such differences in the first and second samples SP01 and SP02 are obtained by modifying the configurations of the layers, etc.

Second Embodiment

Figure 16:
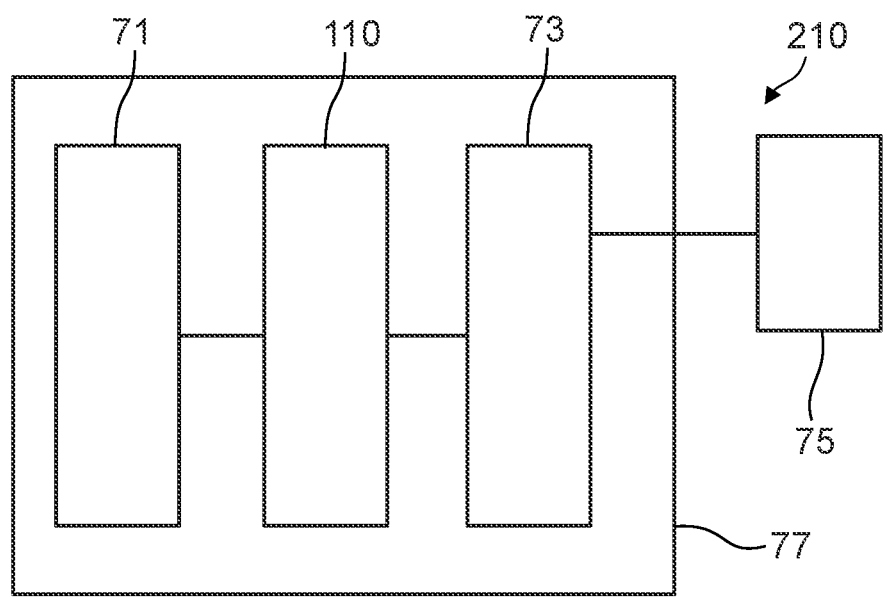
FIG. 16 is a block diagram illustrating a sensor according to a second embodiment.

FIG. 16 is a block diagram illustrating a sensor according to a second embodiment.

As shown in FIG. 16, a sensor module 210 according to the embodiment includes the sensor according to the embodiment (in the example, the sensor 110), a battery 71, a wireless communication circuit 73, an antenna 75, and a housing 77.

For example, the sensor 110, the battery 71, and the wireless communication circuit 73 are located inside the housing 77. At least a portion of the antenna 75 is located outside the housing 77. For example, the housing 77 is mounted to a ground surface, a floor, a wall, etc.

The battery 71 is connected to the sensor 110. The battery 71 is configured to supply electrical power to the sensor 110. The wireless communication circuit 73 is connected to the sensor 110. The wireless communication circuit 73 is configured to transmit a signal corresponding to a value detected by the sensor 110. The antenna 75 is connected with the wireless communication circuit 73. The signal is transmitted via the antenna 75.

Embodiments may include the following configurations (e.g., technological proposals).

Configuration 1

A sensor, comprising:
a base body; and
a first sensor part,
the first sensor part including
a fixed electrode member including a fixed electrode fixed to the base body,
a movable electrode member including a movable electrode, the movable electrode member including a first movable portion, a second movable portion, and a third movable portion between the first movable portion and the second movable portion,
a first support member fixed to the base body and connected with the first movable portion, and
a second support member fixed to the base body and connected with the second movable portion,
the first and second support members supporting the movable electrode member to provide a first gap between the fixed electrode member and the movable electrode member,
the fixed electrode member including
a first fixed electrode portion facing the first movable portion,
a second fixed electrode portion facing the second movable portion, and
a third fixed electrode portion facing the third movable portion,
a third distance along a first direction between the third fixed electrode portion and the third movable portion being less than a first distance along the first direction between the first fixed electrode portion and the first movable portion and less than a second distance along the first direction between the second fixed electrode portion and the second movable portion,
the first direction being from the fixed electrode member toward the movable electrode member.

Configuration 2
 The sensor according to Configuration 1, wherein
 the movable electrode member includes a first movable surface facing the fixed electrode member, and
 the first movable surface is convex.

Configuration 3
 The sensor according to Configuration 2, wherein
 a difference between the third distance and the first distance is not less than 0.1 times a thickness along the first direction of the third movable portion.

Configuration 4
 The sensor according to Configuration 2, wherein
 a difference between the third distance and the first distance is not less than 0.5 times a thickness along the first direction of the third movable portion.

Configuration 5
 The sensor according to any one of Configurations 1 to 4, wherein
 the first support member includes a first fixed part-side portion and a first connection part-side portion,
 the first fixed part-side portion is between the first connection part-side portion and the first movable portion, and
 the distance along the first direction between the base body and the first connection part-side portion is greater than a distance along the first direction between the base body and the first fixed part-side portion.

Configuration 6
 The sensor according to Configuration 5, wherein
 the first support member includes a first fixed part, a first intermediate support part, and a first connection part,
 the first fixed part is fixed to the base body,
 the first connection part is connected with the first movable portion,
 the first intermediate support part is between the first fixed part and the first connection part,
 the first intermediate support part and the first connection part are separated from the base body,
 the first intermediate support part includes the first fixed part-side portion and the first connection part-side portion,
 the first fixed part-side portion is connected with the first fixed part, and
 the first connection part-side portion is connected with the first connection part.

Configuration 7
 The sensor according to Configuration 5 or 6, wherein
 the second support member includes a second fixed part-side portion and a second connection part-side portion,
 the second fixed part-side portion is between the second connection part-side portion and the second movable portion, and
 a distance along the first direction between the base body and the second connection part-side portion is greater than a distance along the first direction between the base body and the second fixed part-side portion.

Configuration 8
 The sensor according to Configuration 7, wherein
 the second support member includes a second fixed part, a second intermediate support part, and a second connection part,
 the second fixed part is fixed to the base body,
 the second connection part is connected with the second movable portion,
 the second intermediate support part is between the second fixed part and the second connection part,
 the second intermediate support part and the second connection part are separated from the base body,
 the second intermediate support part includes the second fixed part-side portion and the second connection part-side portion,
 the second fixed part-side portion is connected with the second fixed part, and
 the second connection part-side portion is connected with the second connection part.

Configuration 9
 The sensor according to any one of Configurations 6 to 8, wherein
 a direction from the first fixed part toward the movable electrode member is along a second direction crossing the first direction,
 a length along a third direction of at least a portion of the first connection part is less than a length along the third direction of the first intermediate support part, and
 the third direction crosses a plane including the first and second directions.

Configuration 10
 The sensor according to any one of Configurations 1 to 9, wherein
 a distance between the fixed electrode member and the movable electrode member is deformable according to a concentration of a first element around the movable electrode member.

Configuration 11
 The sensor according to any one of Configurations 1 to 9, wherein
 at least a portion of the first support member is deformable according to a concentration of a first element around the first support member.

Configuration 12
 The sensor according to any one of Configurations 1 to 11, wherein
 at least one of the first support member or the second support member includes a functional film,
 the functional film includes a second element and a third element,
 the second element includes at least one selected from the group consisting of Pd and Pt, and
 the third element includes Si.

Configuration 13
 The sensor according to Configuration 12, wherein
 the functional film further includes a fourth element, and
 the fourth element includes Cu.

Configuration 14
 The sensor according to any one of Configurations 1 to 13, further comprising:
 a second sensor part,
 the second sensor part including
  a sensor member including a conductive member, the sensor member including a first sensor portion, a second sensor portion, and a third sensor portion between the first sensor portion and the second sensor portion,
  a first support part fixed to the base body and connected with the first sensor portion, and
  a second support part fixed to the base body and connected with the second sensor portion,
 the first and second support parts supporting the sensor member to provide a second gap between the base body and the sensor member.

Configuration 15
  The sensor according to Configuration 14, wherein
  the base body includes:
    a first counter portion facing the first sensor portion;
    a second counter portion facing the second sensor portion; and
    a third counter portion facing the third sensor portion, and
    a third counter distance along the first direction between the third counter portion and the third sensor portion is greater than a first counter distance along the first direction between the first counter portion and the first sensor portion and greater than a second counter distance along the first direction between the second counter portion and the second sensor portion.

Configuration 16
  The sensor according to Configuration 15, wherein
  a difference between the third counter distance and the first counter distance is not less than 0.1 times a thickness along the first direction of the third sensor portion.

Configuration 17
  The sensor according to any one of Configurations 14 to 16, wherein
    the sensor member includes a base body counter surface facing the base body, and
    the base body counter surface is concave.

Configuration 18
  The sensor according to any one of Configurations 14 to 17, further comprising:
    an electrical circuit,
    the electrical circuit being configured to output at least one of a first signal or a second signal,
    the first signal corresponding to an electrical capacitance between the fixed electrode and the movable electrode,
    the second signal corresponding to an electrical resistance of the conductive member.

Configuration 19
  A sensor, comprising:
    a base body; and
    a first sensor part,
    the first sensor part including
      a fixed electrode member including a fixed electrode fixed to the base body,
      a movable electrode member including a movable electrode, the movable electrode member including a first movable portion, a second movable portion, and a third movable portion between the first movable portion and the second movable portion,
      a first support member fixed to the base body and connected with the first movable portion, and
      a second support member fixed to the base body and connected with the second movable portion,
    the first and second support members supporting the movable electrode member to provide a first gap between the fixed electrode member and the movable electrode member,
    the first support member including a first fixed part-side portion and a first connection part-side portion,
    the first connection part-side portion being between the first fixed part-side portion and the first movable portion,
    a distance along the first direction between the base body and the first connection part-side portion being greater than a distance along the first direction between the base body and the first fixed part-side portion.

Configuration 20
  The sensor according to Configuration 19, wherein
    the first support member includes a first fixed part, a first intermediate support part, and a first connection part,
    the first fixed part is fixed to the base body,
    the first connection part is connected with the first movable portion,
    the first intermediate support part is between the first fixed part and the first connection part,
    the first intermediate support part and the first connection part are separated from the base body,
    the first intermediate support part includes the first fixed part-side portion and the first connection part-side portion,
    the first fixed part-side portion is connected with the first fixed part, and
    the first connection part-side portion is connected with the first connection part.

Configuration 21
  The sensor according to Configuration 19 or 20, wherein
    a difference between the distance along the first direction between the base body and the first connection part-side portion and the distance along the first direction between the base body and the first fixed part-side portion is not less than 0.1 times a length along the first direction of the first connection part-side portion.

Configuration 22
  The sensor according to Configuration 20, wherein
    a direction from the first fixed part toward the movable electrode member is along a second direction crossing the first direction,
    a length along a third direction of at least a portion of the first connection part is less than a length along the third direction of the first intermediate support part, and
    the third direction crosses a plane including the first and second directions.

Configuration 23
  A sensor, comprising:
    a base body; and
    a sensor part,
    the sensor part including
      a sensor member including a conductive member, the sensor member including a first sensor portion, a second sensor portion, and a third sensor portion between the first sensor portion and the second sensor portion,
      a first support part fixed to the base body and connected with the first sensor portion, and
      a second support part fixed to the base body and connected with the second sensor portion,
    the first and second support parts supporting the sensor member to provide a second gap between the base body and the sensor member,
    the base body including
      a first counter portion facing the first sensor portion,
      a second counter portion facing the second sensor portion, and
      a third counter portion facing the third sensor portion
      a third counter distance along the first direction between the third counter portion and the third sensor portion being greater than a first counter distance along the first direction between the first counter portion and the first sensor portion and greater than a second counter distance along the first direction between the second counter portion and the second sensor portion.

According to embodiments, a sensor and a sensor module can be provided in which the detection sensitivity can be improved.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as base bodies, fixed electrode members, movable electrode members, support members, sensor members, support portions, electrical circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors and sensor modules practicable by an appropriate design modification by one skilled in the art based on the sensors and the sensor modules described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a base body; and
a first sensor part,
the first sensor part including
a fixed electrode member including a fixed electrode fixed to the base body,
a movable electrode member including a movable electrode, the movable electrode member including a first movable portion, a second movable portion, and a third movable portion between the first movable portion and the second movable portion,
a first support member fixed to the base body and connected with the first movable portion, and
a second support member fixed to the base body and connected with the second movable portion,
the first and second support members supporting the movable electrode member to provide a first gap between the fixed electrode member and the movable electrode member,
the fixed electrode member including
a first fixed electrode portion facing the first movable portion,
a second fixed electrode portion facing the second movable portion, and
a third fixed electrode portion facing the third movable portion,
a third distance along a first direction between the third fixed electrode portion and the third movable portion being less than a first distance along the first direction between the first fixed electrode portion and the first movable portion and less than a second distance along the first direction between the second fixed electrode portion and the second movable portion,
the first direction being from the fixed electrode member toward the movable electrode member.

2. The sensor according to claim 1, wherein
the movable electrode member includes a first movable surface facing the fixed electrode member, and
the first movable surface is convex.

3. The sensor according to claim 2, wherein
a difference between the third distance and the first distance is not less than 0.1 times a thickness along the first direction of the third movable portion.

4. The sensor according to claim 2, wherein
a difference between the third distance and the first distance is not less than 0.5 times a thickness along the first direction of the third movable portion.

5. The sensor according to claim 1, wherein
the first support member includes a first fixed part-side portion and a first connection part-side portion,
the first fixed part-side portion is between the first connection part-side portion and the first movable portion, and
the distance along the first direction between the base body and the first connection part-side portion is greater than a distance along the first direction between the base body and the first fixed part-side portion.

6. The sensor according to claim 5, wherein
the first support member includes a first fixed part, a first intermediate support part, and a first connection part,
the first fixed part is fixed to the base body,
the first connection part is connected with the first movable portion,
the first intermediate support part is between the first fixed part and the first connection part,
the first intermediate support part and the first connection part are separated from the base body,
the first intermediate support part includes the first fixed part-side portion and the first connection part-side portion,
the first fixed part-side portion is connected with the first fixed part, and
the first connection part-side portion is connected with the first connection part.

7. The sensor according to claim 5, wherein
the second support member includes a second fixed part-side portion and a second connection part-side portion,
the second fixed part-side portion is between the second connection part-side portion and the second movable portion, and
a distance along the first direction between the base body and the second connection part-side portion is greater than a distance along the first direction between the base body and the second fixed part-side portion.

8. The sensor according to claim 7, wherein
the second support member includes a second fixed part, a second intermediate support part, and a second connection part,
the second fixed part is fixed to the base body,
the second connection part is connected with the second movable portion,
the second intermediate support part is between the second fixed part and the second connection part,
the second intermediate support part and the second connection part are separated from the base body,
the second intermediate support part includes the second fixed part-side portion and the second connection part-side portion, the second fixed part-side portion is connected with the second fixed part, and the second connection part-side portion is connected with the second connection part.

9. The sensor according to claim 6, wherein
a direction from the first fixed part toward the movable electrode member is along a second direction crossing the first direction,
a length along a third direction of at least a portion of the first connection part is less than a length along the third direction of the first intermediate support part, and
the third direction crosses a plane including the first and second directions.

10. The sensor according to claim 1, wherein
a distance between the fixed electrode member and the movable electrode member is deformable according to a concentration of a first element around the movable electrode member.

11. The sensor according to claim 1, wherein
at least a portion of the first support member is deformable according to a concentration of a first element around the first support member.

12. The sensor according to claim 1, wherein
at least one of the first support member or the second support member includes a functional film,
the functional film includes a second element and a third element,
the second element includes at least one selected from the group consisting of Pd and Pt, and
the third element includes Si.

13. The sensor according to claim 1, further comprising:
a second sensor part,
the second sensor part including
    a sensor member including a conductive member, the sensor member including a first sensor portion, a second sensor portion, and a third sensor portion between the first sensor portion and the second sensor portion,
    a first support part fixed to the base body and connected with the first sensor portion, and
    a second support part fixed to the base body and connected with the second sensor portion,
the first and second support parts supporting the sensor member to provide a second gap between the base body and the sensor member.

14. The sensor according to claim 13, wherein
the base body includes:
    a first counter portion facing the first sensor portion;
    a second counter portion facing the second sensor portion; and
    a third counter portion facing the third sensor portion, and
a third counter distance along the first direction between the third counter portion and the third sensor portion is greater than a first counter distance along the first direction between the first counter portion and the first sensor portion and greater than a second counter distance along the first direction between the second counter portion and the second sensor portion.

15. The sensor according to claim 13, wherein
the sensor member includes a base body counter surface facing the base body, and
the base body counter surface is concave.

16. The sensor according to claim 13, further comprising:
an electrical circuit,
the electrical circuit being configured to output at least one of a first signal or a second signal,
the first signal corresponding to an electrical capacitance between the fixed electrode and the movable electrode,
the second signal corresponding to an electrical resistance of the conductive member.

17. A sensor, comprising:
a base body; and
a first sensor part,
the first sensor part including
    a fixed electrode member including a fixed electrode fixed to the base body,
    a movable electrode member including a movable electrode, the movable electrode member including a first movable portion, a second movable portion, and a third movable portion between the first movable portion and the second movable portion,
    a first support member fixed to the base body and connected with the first movable portion, and
    a second support member fixed to the base body and connected with the second movable portion,
the first and second support members supporting the movable electrode member to provide a first gap between the fixed electrode member and the movable electrode member,
the first support member including a first fixed part-side portion and a first connection part-side portion,
the first connection part-side portion being between the first fixed part-side portion and the first movable portion,
a distance along the first direction between the base body and the first connection part-side portion being greater than a distance along the first direction between the base body and the first fixed part-side portion.

18. The sensor according to claim 17, wherein
the first support member includes a first fixed part, a first intermediate support part, and a first connection part,
the first fixed part is fixed to the base body,
the first connection part is connected with the first movable portion,
the first intermediate support part is between the first fixed part and the first connection part,
the first intermediate support part and the first connection part are separated from the base body,
the first intermediate support part includes the first fixed part-side portion and the first connection part-side portion,
the first fixed part-side portion is connected with the first fixed part, and
the first connection part-side portion is connected with the first connection part.

19. The sensor according to claim 18, wherein
a direction from the first fixed part toward the movable electrode member is along a second direction crossing the first direction,
a length along a third direction of at least a portion of the first connection part is less than a length along the third direction of the first intermediate support part, and
the third direction crosses a plane including the first and second directions.

20. A sensor, comprising:
a base body; and
a sensor part,
the sensor part including
    a sensor member including a conductive member, the sensor member including a first sensor portion, a second sensor portion, and a third sensor portion between the first sensor portion and the second sensor portion, a first support part fixed to the base body and connected with the first sensor portion, and a second support part fixed to the base body and connected with the second sensor portion, the first and second support parts supporting the sensor member to provide a second gap between the base body and the sensor member, the base body including a first counter portion facing the first sensor portion, a second counter portion facing the second sensor portion, and a third counter portion facing the third sensor portion, a third counter distance along the first direction between the third counter portion and the third sensor portion being greater than a first counter distance along the first direction between the first counter portion and the first sensor portion and greater than a second counter distance along the first direction between the second counter portion and the second sensor portion.

* * * * *